(12) United States Patent
Kuang et al.

(10) Patent No.: US 9,226,914 B2
(45) Date of Patent: Jan. 5, 2016

(54) METHODS FOR PROMOTING NEURONAL DEVELOPMENT AND/OR HEALTH

(71) Applicant: Mead Johnson Nutrition Company, Glenview, IL (US)

(72) Inventors: Chenzhong Kuang, Newburgh, IN (US); Yan Xiao, Neburgh, IN (US); Eduard Poels, Newburgh, IN (US); Zeina Jouni, Evansville, IN (US); Dirk Hondmann, Winnetka, IL (US)

(73) Assignee: Mead Johnson Nutrition Company, Glenview, IL (US)

( * ) Notice: Subject to any disclaimer, the term of this patent is extended or adjusted under 35 U.S.C. 154(b) by 138 days.

(21) Appl. No.: 13/942,827

(22) Filed: Jul. 16, 2013

(65) Prior Publication Data

US 2015/0023923 A1 Jan. 22, 2015

(51) Int. Cl.
| | |
|---|---|
| *A23L 1/29* | (2006.01) |
| *A23L 1/30* | (2006.01) |
| *A23C 9/13* | (2006.01) |
| *A61K 9/00* | (2006.01) |
| *A61K 31/202* | (2006.01) |
| *A61K 35/00* | (2006.01) |
| *A61K 31/385* | (2006.01) |
| *A61K 31/7012* | (2006.01) |
| *A61K 38/40* | (2006.01) |
| *A23C 9/20* | (2006.01) |
| *A23L 1/305* | (2006.01) |

(52) U.S. Cl.
CPC ............ *A61K 31/385* (2013.01); *A23C 9/20* (2013.01); *A23L 1/296* (2013.01); *A23L 1/3008* (2013.01); *A23L 1/3056* (2013.01); *A61K 31/202* (2013.01); *A61K 31/7012* (2013.01); *A61K 35/00* (2013.01); *A61K 38/40* (2013.01); *A23V 2002/00* (2013.01)

(58) Field of Classification Search
CPC ........... A61K 2300/00; A23V 2250/00; A23V 2250/28; A23V 2250/282; A23V 2250/54; A23V 2250/02; A23V 2250/18; A23V 2250/1868; A23V 2250/1862; A23V 2250/5438; A23V 2200/322; A23L 1/29; A23L 1/296; A23L 1/293; A23L 1/30; A23L 1/305; A23L 1/3008; A23L 1/301
See application file for complete search history.

(56) References Cited

U.S. PATENT DOCUMENTS

| | | | |
|---|---|---|---|
| 5,374,567 | A | 12/1994 | Cartagena |
| 5,397,591 | A | 3/1995 | Kyle |
| 5,550,156 | A | 8/1996 | Kyle |
| 5,849,885 | A | 12/1998 | Nuyens |
| 5,861,491 | A | 1/1999 | Nuijens |
| 5,919,913 | A | 7/1999 | Nuyens |
| 6,620,326 | B1 | 9/2003 | Lihme et al. |
| 6,977,046 | B2 | 12/2005 | Hubbuch et al. |
| 7,368,141 | B2 | 5/2008 | Lihme |
| 7,812,138 | B2 | 10/2010 | Lihme et al. |
| 2005/0107338 | A1 | 5/2005 | Seidman |
| 2008/0003330 | A1 | 1/2008 | Rueda et al. |
| 2011/0288016 | A1* | 11/2011 | Hageman ....................... 514/7.3 |
| 2012/0136220 | A1 | 5/2012 | Reynolds |
| 2012/0184484 | A1 | 7/2012 | Wang et al. |
| 2012/0219526 | A1 | 8/2012 | Klassen et al. |
| 2013/0150306 | A1* | 6/2013 | Wittke .......................... 514/17.5 |
| 2013/0172286 | A1* | 7/2013 | Gil Hernandez et al. ....... 514/48 |
| 2014/0179775 | A1 | 6/2014 | Kuang et al. |

FOREIGN PATENT DOCUMENTS

| | | | |
|---|---|---|---|
| CN | 102318827 | 1/2012 | |
| EP | 2258218 | 12/2010 | |
| EP | 2609814 | 7/2013 | |
| GB | 2327347 | 1/1999 | |
| WO | 9200799 | 1/1992 | |
| WO | 9717132 | 5/1997 | |
| WO | 0218237 | 3/2002 | |
| WO | WO 2011069987 A1 * | 6/2011 | ............. A23C 17/00 |
| WO | 2014109862 | 7/2014 | |

OTHER PUBLICATIONS

Pereira, D.I.A. et al. 2003. An in vitro study of the probiotic potential of a bile-salt-hydrolyzing Lactobacillus fermentum strain, and determination of its cholesterol-lowering properties. Applied and Environmental Microbiology 69(8): 4743-4752. specif. pp. 4743-4744.*
PubChem. alpha-Lipoic acid. Datasheet [online]. NCBI, NIH. Create date: Sep. 16, 2004. [retrieved on Sep. 11, 2014]. Copyright NCBI. NLM.NIH. Bethesda, MD. Retrieved from the Internet: <URL: http://pubchem.ncbi.nlm.nih.gov/summary/summary.cgi?cid=864&loc=ec_rcs>. pp. 1-6.*
PubChem. Arachidonic acid. Datasheet [online]. NCBI, NIH. Create date: Sep. 16, 2004. [retrieved on Sep. 11, 2014]. Copyright NCBI. NLM.NIH. Bethesda, MD. Retrieved from the Internet: <URL: http://pubchem.ncbi.nlm.nih.gov/summary/summary.cgi?cid=444899&loc=ec_rcs>. pp. 1-5.*
PubChem. Sialic acid. Datasheet [online]. NCBI, NIH. Create date: Jun. 24, 2005. [retrieved on Sep. 11, 2014]. Copyright NCBI.NLM. NIH. Bethesda, MD. Retrieved from the Internet: <URL: http://pubchem.ncbi.nlm.nih.gov/summary/summary.cgi?cid=445063&loc=ec_rcs>. pp. 1-4.*

(Continued)

*Primary Examiner* — John S Brusca
*Assistant Examiner* — Sharon M Papciak
(74) *Attorney, Agent, or Firm* — Patterson Intellectual Property Law, P.C; James R. Cartiglia; Bethany J. Whelan

(57) ABSTRACT

Disclosed are methods for promoting neuronal health and/or development in a subject by providing nutritional compositions comprising docosahexaenoic acid and alpha-lipoic acid. The nutritional composition may further include lactoferrin, a prebiotic, a probiotic, and mixtures thereof. Additionally disclosed are methods for accelerating the development of neuronal activity and/or strengthening electrochemical synapse signaling by providing the nutritional composition(s) disclosed herein to a target subject.

19 Claims, 14 Drawing Sheets
(11 of 14 Drawing Sheet(s) Filed in Color)

(56) References Cited

OTHER PUBLICATIONS

Borcea, V., et al., "a-Lipoic Acid Decreases Oxidative Stress Even in Diabetic Patients with Poor Glycemic Control and Albuminuria," Free Radical Biology & Medicine, vol. 22, Nos. 11/12, pp. 1495-1500, 1999.

Gleiter, C., et al., "Influence of food intake on the bioavailability of thioctic acid enantiomers," Eur J. Clin. Pharmacol (1996) 50: 513-514.

Harris, J.J., et al., "The Energetics of CNS White Matter," J. Neurosci., Jan. 4, 2012; 32(1): 356-371.

Jordan, S., et al., "A New Metabolic Link. The Acyl carrier protein of lipid synthesis donates lipoic acid to the pyruvate dehydrogenase complex in *Escherichia Coli* and Mitochondria," The Journal of Biological Chemistry, vol. 272, No. 29, Issue of Jul. 18, pp. 17903-17906, 1997.

Mehta, S., et al., "Molecular targets in cerebral ischemia for developing novel therapeutics," Brain Research Reviews 54 (2007) 34-66.

Reed, L.J., "Crystalline a-Lipoic Acid: A Catalytic Agent Associated with Pyruvate Dehydrogenase," Science, New Series, vol. 114, No. 2952 (Jul. 27, 1951), pp. 93-94.

Shay, K., et al., "Alpha-Lipoic Acid as a dietary supplement: Molecular mechanisms and therapeutic potential," Biochim Biophys Acta. Oct. 2009; 1790(10): 1149-1160.

Singh, U., et al., "Alpha-Lipoic acid supplementation and diabetes," Nutr Rev. Nov. 2008; 66(11): 646-657.

Packer, L., et al., "Alpha-Lipoic Acid as a Biological Antioxidant," Free Radical Biology & Medicine, vol. 19, No. 2, pp. 227-250, 1995.

Yadomae, T., "Structure and Biological Activities of Fungal B-1, 3-Glucans," Yakugaku Zasshi 2000;120:413-431.

Yamada, T., et al., "a-Lipoic acid (LA) enantiomers protect SH-SY5Y cells against glutathione depletion," Neurochemistry International, 59(7):1003-1009, Dec. 2011.

Ziegler, D., et al., "Treatment of Symptomatic Diabetic Polyneuropathy With the Antioxidant a-Lipoic Acid," Diabetes Care 22:1296-1301, 1999.

Suchy, J. et al., "Dietary supplementation with a combination of alpha-lipoic acid, acetyl-l-carnitine, glycerophosphocoline, docosahexaenoic acid, and phosphatidylserine reduces oxidative damage to murine brain and improves cognitive performance," Nutrition Research 29 (2009) 70-74.

"Report of the American Institute of Nutrition Ad Hoc Committee on Standards for Nutritional Studies," The Journal of Nutrition, American Society for Nutrition, U.S., vol. 107, No. 7, Jul. 1977.

Mackenzie, G., et al., "A deficit in zinc availability can cause alterations in tubulin thiol redox status in cultured neurons and in developing fetal rat brain," Free Radical Biology & Medicine 51 (2011) 480-489.

Chauhan, N., et al., "Amelioration of Early Cognitive Deficits by Aged Garlic Extract in Alzheimer's Transgenic Mice," Phytother. Res. 21, 629-640 (2007).

\* cited by examiner

FIG. 3A

DHA
Control activity 10 nM

Lipoic acid
Control activity

100 µM 5 mM

METHODS FOR PROMOTING NEURONAL DEVELOPMENT AND/OR HEALTH

TECHNICAL FIELD

The present disclosure relates to method(s) for promoting neuronal health and development, as well as accelerating the development of neuronal activity and/or improving electrochemical synapse signaling, comprising providing a nutritional composition including alpha-lipoic acid ("ALA") and docosahexaenoic acid ("DHA"). The methods disclosed herein include nutritional compositions suitable for administration to adult and pediatric subjects.

BACKGROUND

The brain makes up only 2% of total body weight, yet it is a demanding organ that uses up to 30% of the day's calories and nutrients. (Harris, J. J. et al, *The Energetics of CNS White Matter*. Jour. of. Neuroscience, January 2012: 32(1): 356-371). The human brain and nervous system begin forming very early in prenatal life and both continue to develop until about the age of three. This early development can have lifelong effects on overall brain and nervous system health. Accordingly, brain nutrients can be important additives in the diets of infants, children and pregnant and lactating women because of their ability to promote early brain development and prevent and protect from brain and nervous system injury or illness. Additionally, brain nutrients are important for adults, as many nutrients promote nervous system repair and provide neuroprotective health benefits.

Numerous nutrients are believed to be involved with supporting healthy brain development. Recently, however, it has been discovered herein that ALA, which is also commonly known as lipoic acid ("LA"), may accelerate the development of neuronal activity thus enhancing neuronal development and cognitive function.

Given the early development of the nervous system, what is needed is a method for promoting neuronal health and development, in order to support brain and nervous system health. Accordingly, provided herein are methods for accelerating the development of neuronal activity and/or improving electrochemical synapse signaling in a target subject by providing a nutritional composition comprising ALA. Moreover, these nutritional compositions may have additive and/or synergistic nervous system health benefits.

BRIEF SUMMARY

Briefly, the present disclosure is directed, in an embodiment, to a method for promoting neuronal development by providing a nutritional composition comprising ALA and DHA. In some embodiments, the nutritional composition may also comprise lactoferrin, at least one prebiotic, at least one probiotic, and mixtures thereof. It is believed that DHA may act synergistically with ALA to accelerate neuronal activity and/or promote and strengthen electrochemical synapse signaling in a subject.

In certain embodiments the nutritional composition may further comprise at least one additional long chain polyunsaturated fatty acid ("LCPUFA") other than DHA, sialic acid, a prebiotic source, a probiotic source, β-glucan, an iron source, and/or mixtures of one or more thereof.

Due to critical brain development during the first years of life, in some embodiments the nutritional composition provided comprises an infant formula or a pediatric nutritional composition. Additionally, the nutritional compositions described herein may be useful as medicaments or nutritional supplements for promoting neurological health in subjects with a neural degenerative diseases and/or brain injury. Further, the nutritional compositions of the present disclosure may provide neuroprotective health benefits and promote overall brain and nervous system health.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B display a qualitative comparison of effects induced by DHA or alpha-lipoic acid, as illustrated by in vitro spike trains for 19 neurons over 60 seconds of selected concentrations for both DHA and ALA, respectively.

DETAILED DESCRIPTION

Figure 1:
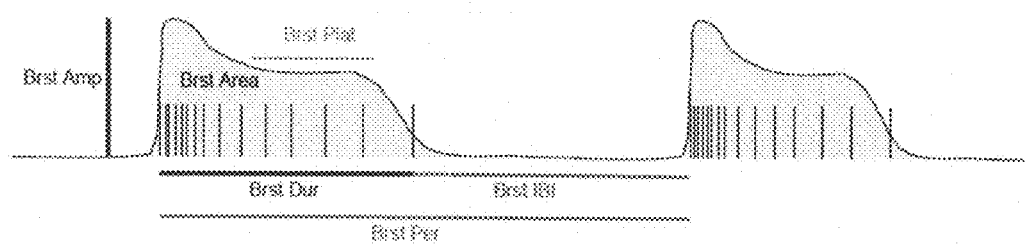
FIG. 1 provides an example illustration of a few of the burst parameters described herein.

Reference now will be made in detail to the embodiments of the present disclosure, one or more examples of which are set forth herein below. Each example is provided by way of explanation of the nutritional composition and methods of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to a method for promoting neuronal health and development, by providing a nutritional composition comprising DHA and ALA. Additionally, the disclosure relates to methods of accelerating the development of neuronal activity and/or strengthening or improving electrochemical synapse signaling, by providing a target subject a nutritional composition containing ALA. Further disclosed are, methods for supporting and promoting brain and nervous system health, neurogenesis and/or cognitive development.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults. The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Alpha-lipoic acid", abbreviated "ALA" herein, refers to an organosulfur compound derived from octanoic acid having the molecular formula $C_8H_{14}S_2O_2$. Generally, ALA contains two sulfur atoms attached via a disulfide bond. As used herein the terms "lipoic acid", abbreviated "LA", and "alpha-lipoic acid", abbreviated "ALA", and their respective abbreviations may be used interchangeably.

The term "degree of hydrolysis" refers to the extent to which peptide bonds are broken by a hydrolysis method. For example, the protein equivalent source of the present disclosure may, in some embodiments comprise hydrolyzed protein having a degree of hydrolysis of no greater than 40%. For this example, this means that at least 40% of the total peptide bonds have been cleaved by a hydrolysis method.

The term "extensively hydrolyzed" means having a degree of hydrolysis which is greater than or equal to 50%.

The term "partially hydrolyzed" means having a degree of hydrolysis which is less than 50%.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the $37^{th}$ week of gestation. "Full term" means an infant born after the end of the $37^{th}$ week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts at least one beneficial effect on the health of the host.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

The term "cell equivalent" refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc.

"Prebiotic" means a non-digestible food ingredient that beneficially affects the host by selectively stimulating the growth and/or activity of one or a limited number of bacteria in the digestive tract that can improve the health of the host.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

As used herein, "non-human lactoferrin" means lactoferrin which is produced by or obtained from a source other than human breast milk. In some embodiments, non-human lactoferrin is lactoferrin that has an amino acid sequence that is different than the amino acid sequence of human lactoferrin. In other embodiments, non-human lactoferrin for use in the present disclosure includes human lactoferrin produced by a genetically modified organism. The term "organism", as used herein, refers to any contiguous living system, such as animal, plant, fungus or micro-organism.

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The development of the brain and nervous system plays a crucial role in the overall health and well-being of an individual. Accordingly, the method(s) of the present disclosure promotes brain and nervous system health. In certain embodiments, the method disclosed herein provides a nutritional composition comprising ALA and DHA that accelerates the development of neuronal activity and/or improves electrochemical synapse signaling in a target subject, as compared to neuronal activity when these nutrients are not provided. Accordingly, the nutritional composition(s) comprise ALA and DHA, and may be provided according to the method(s) described herein. Without being bound by any particular theory, this combination of DHA and ALA may have additive and/or synergistic beneficial effects that support brain and nervous system development and health.

Examples of ALA suitable for use in the nutritional composition(s) described herein include, but are not limited to, enantiomers and racemic mixtures of ALA, including, RLA, SLA, and R/S-LA. Also suitable is R-lipoic acid stabilized with either sodium ("Na-RALA") or potassium as potassium-R-lipoate. As used herein, ALA may include at least one of its pharmaceutically acceptable salts, metabolites, and/or combinations thereof.

In some embodiments the nutritional composition may be formulated with an effective amount of ALA. As used for this embodiment effective amount means an amount for producing beneficial effects on a subject when administered. In some embodiments, an effective amount of ALA includes an amount to accelerate the development of neuronal activity and/or improve electrochemical synapse signaling when provided to a target subject. For example, in some embodiments, an effective amount of ALA is from about 0.1 mg/100 kcals to about 35 mg/100 kcals. In some embodiments, ALA may be present in an amount from about 2.0 mg/100 kcals to about 25 mg/100 kcals. In still other embodiments, ALA may be present in an amount from about 5.0 mg/100 kcals to about 15 mg/100 kcals.

In some embodiments the nutritional composition may be formulated with an effective amount of DHA. As used for this embodiment effective amount means an amount for producing beneficial effects on a subject when administered. In some embodiments, an effective amount of DHA includes an amount necessary to accelerate the development of neuronal activity and/or improve electrochemical synapse signaling when provided to a target subject. Without being bound by any particular theory, it is believe that the combination of DHA and ALA may synergistically promote neuronal development, including accelerating neuronal activity and/or electrochemical synapse signaling, as compared to neuronal development or activity when DHA and ALA are not provided.

The nutritional composition of the present disclosure may also contain at least one additional long chain polyunsaturated fatty acids ("LCPUFAs") other than DHA. Suitable additional LCPUFAs include, but are not limited to eicosapentaenoic acid ("EPA"), arachidonic acid ("ARA"), linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

The amount of LCPUFAs, which may include DHA, in the nutritional composition may be from about 5 mg/100 kcal to about 100 mg/100 kcal. In some embodiments the LCPUFA concentration of the nutritional composition may be from about 10 10 mg/100 kcal to about 50 mg/100 kcal. Still in some embodiments, the LCPUFA concentration of the nutritional composition may be from about 15 mg/100 kcal to about 30 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional composition. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional composition in the form of esters of free fatty acids; mono-, di- and tri-glycerides; phosphoglyerides, including lecithins; and/or mixtures thereof. Additionally, LCPUFA may be provided in the nutritional composition in the form of phospholipids, especially phosphatidylcholine.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the weight ratio of ARA:DHA is from about 1:2 to about 4:1.

DHA is, in some embodiments, present in the nutritional composition from about 5 mg/100 kcal to about 75 mg/100 kcal. In some embodiments, DHA is present from about 10 mg/100 kcal to about 50 mg/100 kcal. In still some embodiments, DHA is present in the nutritional composition from about 15 mg/100 kcal to about 30 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. The enhanced level of DHA of the nutritional composition may compensate for an existing nutritional DHA deficit.

In some embodiments, lactoferrin may also be provided in the nutritional composition. Lactoferrins are single chain polypeptides of about 80 kD containing 1-4 glycans, depending on the species. The 3-D structures of lactoferrin of different species are similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms.

Lactoferrin for use in the present disclosure may be, for example, isolated from the milk of a non-human animal or produced by a genetically modified organism. More specifically, the lactoferrin for use herein can, in some embodiments comprise non-human lactoferrin, non-human lactoferrin produced by a genetically modified organism and/or human lactoferrin produced by a genetically modified organism.

Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 65% homology with human lactoferrin and in some embodiments, at least 75% homology. Non-human lactoferrins acceptable for use in the present disclosure include, without limitation, bLF, porcine lactoferrin, equine lactoferrin, buffalo lactoferrin, goat lactoferrin, murine lactoferrin, camel lactoferrin and combinations thereof.

bLF suitable for the present disclosure may be produced by any method known in the art. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

The lactoferrin that is employed herein may, in some embodiments, be lactoferrin isolated from whole milk and/or milk having a low somatic cell count, wherein "low somatic cell count" refers to a somatic cell count less than 200,000 cells/mL. By way of example, suitable lactoferrin is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Surprisingly, lactoferrin included herein maintains certain bactericidal activity even if exposed to a low pH (i.e., below about 7, and even as low as about 4.6 or lower) and/or high temperatures (i.e., above about 65° C., and as high as about 120° C.), conditions which would be expected to destroy or severely limit the stability or activity of human lactoferrin. These low pH and/or high temperature conditions can be expected during certain processing regimen for nutritional compositions of the types described herein, such as pasteurization. Therefore, even after processing regimens, lactoferrin has bactericidal activity against undesirable bacterial pathogens found in the human gut.

When incorporated into a nutritional composition for practicing the method of the present disclosure, in some embodiments lactoferrin is present in an amount from about 10 mg/100 kcal to about 250 mg/100 kcal. Still in some embodiments, lactoferrin is present in the nutritional composition in an amount of from about 50 mg/100 kcal to about 175 mg/100 kcal. In some embodiments, lactoferrin is present in an amount from about 100 mg/100 kcal to about 150 mg/100 kcal.

In some embodiments, the nutritional composition may comprise an effective amount of ALA and DHA. As used in this embodiment effective amount means an amount for producing beneficial effects on a subject when administered. In some embodiments, the effective amount of a combination of ALA and DHA includes the amount of each nutrient, in combination, necessary to accelerate the development of neuronal activity and/or promote and strengthen electrochemical synapse signaling when provided to a target subject, as compared to neuronal activity or electrochemical synapse signaling that occurs outside the presence of a combination of ALA and DHA.

In the methods described herein the nutritional composition(s) may be formulated with other ingredients in order to provide appropriate nutrient levels for target subjects. In some embodiments, the nutritional composition is a nutritionally complete formula that is suitable to support normal growth and also accelerate brain development. In certain other embodiments, the composition and concentration of the nutrients are designed to mimic levels that are healthy for early human development.

Additionally, the nutrients ALA and DHA may be added or incorporated into the nutritional composition by any method well known in the art. In some embodiments, they may be added to a nutritional composition to supplement the nutritional composition. For example, in some embodiments, ALA and/or DHA may be added to a commercially available infant formula. For example, Enfalac, Enfamil®, Enfamil® Premature Formula, Enfamil® with Iron, Enfamil® LIPIL®, Lactofree®, Nutramigen®, Pregestimil®, and ProSobee® (each of which is available from Mead Johnson Nutrition Company, Glenview, Ill., U.S.) may be supplemented with suitable levels of ALA and DHA, and used in the practice of the present disclosure.

In other embodiments, certain nutrient sources containing ALA and/or DHA may be selected and incorporated in the nutritional composition described herein by any method known in the art. For example, a certain amount of a fat source including ALA and/or DHA may be selected and either incorporated into a nutritional composition or may be substituted with another fat source that does not contain ALA and/or DHA. In still other embodiments, the source of an ingredient typically added to a nutritional composition may be altered, such that the source chosen provides both the ingredient that is commonly added to the nutritional composition and ALA and/or DHA.

In some embodiments, ALA and DHA may be included in prenatal dietary supplements by any method known in the art. The prenatal administration of a combination of ALA and DHA may directly impact the neurological development of the fetus and embryo. Since brain development begins early in prenatal life, the inclusion of ALA and DHA in a prenatal dietary supplement may accelerate the development of neuronal networks while the pediatric subject is still in utero.

Conveniently, commercially available prenatal dietary supplements and/or prenatal nutritional products may be used. For example, Expecta® Supplement (available from Mead Johnson Nutrition Company, Glenview, Ill., U.S.) may be supplemented with suitable levels of ALA and DHA, and used in practice of the present disclosure.

The prenatal dietary supplement may be administered in one or more doses daily. In some embodiments, the prenatal dietary supplement is administered in two doses daily. In a separate embodiment, the prenatal dietary supplement is administered in three daily doses. The prenatal dietary supplement may be administered to either pregnant women or women who are breastfeeding.

Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof. Alternatively, the prenatal dietary supplement of the present disclosure may be added to a more complete nutritional composition. In this embodiment, the nutritional composition may contain protein, fat, and carbohydrate components and may be used to supplement the diet or may be used as the sole source of nutrition.

In some embodiments, the nutritional composition comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Moreover, the nutritional composition(s) of the disclosure may comprise at least one protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein source per 100 kcal. In other embodiments, the nutritional composition comprises between about 3.5 g and about 4.5 g of protein per 100 kcal.

In some embodiments, the proteins of the nutritional composition are provided as intact proteins. In other embodiments, the proteins are provided as a combination of both intact proteins and hydrolyzed proteins, with a degree of hydrolysis of between about 4% and 10%. In certain other embodiments, the proteins are more hydrolyzed. In still other embodiments, the protein source comprises amino acids. In yet another embodiment, the protein source may be supplemented with glutamine-containing peptides.

In some embodiments, the protein source of the nutritional composition comprises either partially or extensively hydrolyzed protein, such as protein from cow's milk. In some embodiments, where the protein source comprises extensively hydrolyzed protein, the nutritional composition may consist essentially of extensively hydrolyzed protein in order to minimize the occurrence of food allergy. Generally, proteins may be treated with enzymes to break down some or most of the proteins that cause adverse symptoms with the goal of reducing allergic reactions, intolerance, and sensitization. Moreover, the proteins may be hydrolyzed by any method known in the art.

In some embodiments, the nutritional composition of the present disclosure is substantially free of intact proteins. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

The nutritional composition may be protein-free in some embodiments and comprise free amino acids as a protein equivalent source. In some embodiments, the term "protein equivalent source" as used herein includes functional equivalents of protein(s), which exert beneficial health effects on a target subject without containing any intact protein. For example, "protein equivalent source" may include certain peptides and/or peptide fractions, amino acids, and combinations thereof. In certain embodiments, the protein source or sources incorporated into the nutritional composition may include both an intact protein source and protein equivalent source.

If included, in some embodiments the protein equivalent source may comprise amino acids. The amino acids included may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized. The amount of free amino acids in the nutritional composition may vary from about 1 g/100 kcal to about 5 g/100 kcal.

The nutritional composition may also comprise a fat source. Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids may be found in milk, such as bovine and caprine. In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 kcals to about 45 mg/100 kcal. In some embodiments sialic acid may be present in an amount from about 5 mg/100 kcals to about 30 mg/100 kcals. In still other embodiments, sialic acid may be present in an amount from about 10 mg/100 kcals to about 25 mg/100 kcals.

The nutritional composition may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising polydextrose ("PDX") and/or galacto-oligosaccharide ("GOS"). In some embodiments, the prebiotic component comprises at least 20% GOS, PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional composition may be from about 0.1 mg/100 kcal to about 0.5 mg/100 kcal or about 0.3 mg/100 kcal.

If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal. In other embodiments, the amount of GOS in the nutritional composition may be from about 0.1 mg/100 kcal to about 1.0 mg/100 kcal or from about 0.1 mg/100 kcal to about 0.5 mg/100 kcal.

In a particular embodiment of the nutritional composition, PDX is administered in combination with GOS. In this embodiment, PDX and GOS can be administered in a ratio of PDX:GOS of between about 9:1 and 1:9. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio of PDX to GOS can be about 8:2.

In a particular embodiment, GOS and PDX are supplemented into the nutritional composition in a total amount of at least about 0.2 mg/100 kcal or about 0.2 mg/100 kcal to about 1.5 mg/100 kcal. In some embodiments, the nutritional composition may comprise GOS and PDX in a total amount of from about 0.6 to about 0.8 mg/100 kcal.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{10}$ cfu of probiotic(s) per 100 kcal. In some embodiments, the amount of probiotic may be from about $1\times10^6$ to about $1\times10^9$ cfu of probiotic(s) per 100 kcal. In certain other embodiments the amount of probiotic may vary from about $1\times10^7$ to about $1\times10^8$ cfu of probiotic(s) per 100 kcal.

The probiotic(s) as used in the nutritional composition(s) disclosed herein may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents. In included in the nutritional composition, the amount of the probiotic cell equivalents may vary from about $1\times10^4$ to about $1.5\times10^{10}$ cell equivalents of probiotic(s) per 100 kcal. In some embodiments the amount of probiotic cell equivalents may be from about $1\times10^6$ to about $1\times10^9$ cell equivalents of probiotic(s) per 100 kcal nutritional composition. In certain other embodiments the amount of probiotic cell equivalents may vary from about $1\times10^7$ to about $1\times10^8$ cell equivalents of probiotic(s) per 100 kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

In some embodiments, the amount of β-glucan in the nutritional composition is between about 3 mg/100 kcal and about 17 mg/100 kcal. In another embodiment the amount of β-glucan is between about 6 mg/100 kcal and about 17 mg/100 kcal.

The nutritional composition may comprise in some embodiments β-1,3;1,6-glucan. The β-1,3;1,6-glucan can be derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

The disclosed nutritional composition described herein, can, in some embodiments also comprise an effective amount of iron. The iron may comprise encapsulated iron forms, such as encapsulated ferrous fumarate or encapsulated ferrous sulfate or less reactive iron forms, such as ferric pyrophosphate or ferric orthophosphate.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 300 µm.

If the nutritional composition is in the form of a ready-to-use product, the osmolality of the nutritional composition may be between about 100 and about 1100 mOsm/kg water, more typically about 200 to about 700 mOsm/kg water.

In certain embodiments, the nutritional composition is hypoallergenic. In other embodiments, the nutritional composition is kosher and/or halal. In still further embodiments, the nutritional composition contains non-genetically modified ingredients. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DR1) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional composition(s) may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM (citric acid esters of mono- and diglycerides of fatty acids), and mixtures thereof.

The present disclosure further provides a method for promoting brain and nervous system health by providing a nutritional composition comprising ALA to a target subject. Without being bound by any particular theory, it is believed that providing a nutritional composition comprising ALA will promote overall neuronal health and/or development. In some embodiments, the nutritional composition provided further comprises DHA.

In some embodiments the target subject may be a pediatric subject. Further, in one embodiment, the nutritional composition provided to the pediatric subject may be an infant formula. Still in some embodiments, the ALA added to the infant formula may be selected from a specific source and concentrations thereof may be adjusted to maximize health benefits. In another embodiment of this method, the nutritional composition comprising ALA that is provided to a pediatric subject is a growing up milk.

In another embodiment the nutritional composition may be provided to a target subject who has suffered, is currently suffering from, or is likely to suffer in the future from a brain and/or nervous system injury. In yet another embodiment, the nutritional composition comprising ALA may be provided to any target subject to promote neuroprotection. In still other embodiments, the method is directed toward promoting neuronal activity of a fetus by providing a nutritional composition comprising ALA to a pregnant or lactating mother. Additionally, the nutritional compositions comprising ALA as described herein may provide a supplemental source of neurological nutrition to target subjects.

The present disclosure further provides a method for promoting neuronal health and/or development, as well as other benefits enumerated herein, and includes administering to the subject an effective amount of the nutritional composition of the present disclosure. The nutritional composition may be expelled directly into a subject's intestinal tract. In some embodiments, the nutritional composition is expelled directly into the gut. In some embodiments, the composition may be formulated to be consumed or administered enterally.

In some embodiments, the methods herein include promoting neuronal network activity by administering to a target subject a nutritional composition including ALA. In some embodiments, the nutritional composition may also include DHA, lactoferrin and mixtures thereof. Also provided are methods for accelerating the development of neuronal activity in a target subject, the method comprising providing a nutritional composition described herein, which includes ALA. Further, the nutritional composition provided to the target subject may include DHA, lactoferrin and combinations thereof.

Still in some embodiments, the disclosure provides a method for strengthening neurological electrochemical connections via administering a nutritional composition comprising ALA and DHA to a target subject. The target subject may include an infant or pediatric subject, and may further include a fetus. In embodiments, where the target subject is a fetus, the mother may ingest the nutritional composition, including but not limited to a prenatal nutritional composition as described herein. Additionally, in some embodiments, after birth of the fetus, a breast-feeding mother may ingest the nutritional composition disclosed herein, which includes ALA, for accelerating the development of neuronal activity in a breast-fed infant.

The methods of the present disclosure directed toward providing the nutritional compositions described herein deliver enhanced neurological nutritional and health benefits to their target subjects. The disclosure of the methods for providing the nutritional composition described herein for a particular neurological illness or to a particular target subject are not to be limiting, instead they further serve as examples where administration of the nutritional composition described herein may be appropriate.

EXAMPLES

Examples are provided to illustrate the neuronal effects of the nutrients included in the nutritional composition(s) described herein. Briefly, neuronal activity patterns were collected when neuronal stem cells were exposed to alpha-lipoic acid, DHA, and combinations thereof according to the procedure described herein. These examples should not be interpreted as any limitation on the nutritional compositions disclosed herein, but serve as illustrations of accelerated neuronal activity and promotion of neuronal synaptic activity of the nutritional composition(s) described herein. It is intended that the specification, together with the example, be considered to be exemplary only, with the scope and spirit of the disclosure being indicated by the claims which follow the examples.

Example 1

This example describes the acute functional effects on neuronal networks of ALA alone and in synergy with DHA. The results indicate the capability of ALA to modulate neuronal network activity, which is revealed by an immediate response of the neuronal activity pattern upon application of ALA and/or DHA to the culture.

Without being bound by any particular theory, the in vitro property described in Example 1 will translate to an in vivo effect, i.e. a capability to modulate brain function such as synaptic strength. Moreover, the calculation of effective concentrations of both ALA and DHA and the synergistic potency thereof can be translated to the in vivo situation.

ALA was purchased from Sigma-Aldrich®, St. Louis, Mo. (#T1395, Lot 071M0191V, CAS No. 1077-28-7). ALA was diluted in 100% to a stock solution of 100 mM and stored at $-20°$ C.

DHA was purchased from Sigma-Aldrich®, St. Louis, Mo. (#D2534, Lot SLBB6915V, CAS No. 6217-54-5). DHA was diluted in 100% to a stock solution of 100 mM and stored at $-20°$ C.

Human recombinant brain derived neurotrophic factor ("hBDNF") was purchased from PeproTech, (#450-02, Lot 051061). The hBDNF was diluted in water to a stock solution concentration of 100 µg/mL and stored at $-20°$ C.

The experiments were performed according to the SOPs, "SOP Preparation Frontal Cortex Mouse—Serum (Rev. 07 2012 Mar. 6 eng)", "SOP Solutions for Neuronal Cell Culture (Rev. 04 2009 Nov. 18 eng)", "SOP Cleaning and Substrate Preparations of MEAs (Rev. 03 2009 Apr. 26 eng)", "SOP Feeding neuronal cell culture", "SOP Cell culture preparation MEAs", "SOP Plexon Recording" and "SOP Plexon Data Analysis".

The microelectrode array neurochips ("MEA neurochips") were provided by the Center for Network Neuroscience (CNNS) at the University of North Texas. These 5×5 $cm^2$ glass chips have a dual recording matrix with 32 passive electrodes per matrix and indium tin oxide conductors. The hydrophobic insulation material surface was activated by a brief butane flame pulse through a stainless steel mask. Thus, cell attachment on a confined region, a 5 mm diameter centered on the electrode array, is ensured. The activated face regions were coated with 25 µg/mL poly-D-lysine (30-70 kD) and incubated overnight in 16 µg/mL laminin for 3 hours right before the preparation.

Frontal cortex tissue was harvested from embryonic day 15 chr:NMRI mice. Mice were sacrificed by cervical dislocation according to the German Animal Protection Act Section 4. Cultures on MEAs were incubated at 37 deg. C. in a 10% $CO_2$ atmosphere until ready for use, which usually is four weeks to three months after seeding. Culture media were replenished two times a week with DMEM containing 10% heat inactivated horse serum. The developing co-cultures were treated with the mitosis inhibitor 5-fluoro-2'-deoxyuridine (25 µMolar) and uridine (63 µMolar) for 48 hours on day 5 after seeding to prevent further glial proliferation.

After establishing a stable activity pattern after 4 weeks, the neuronal networks on MEA chips were employed for substance testing. For this example, cultures between 25 and 38 days in vitro were used. For extracellular recording, MEA neurochips were placed into sterilized constant-bath recording chambers and maintained at 37 deg. C. Recordings were made in DMEM including 10% heat inactivated horse serum. The pH was maintained at 7.4 with a continuous stream of filtered, humidified airflow with 10% $CO_2$. Sets of preamplifiers were positioned to either side of the recording chamber. Recording was performed with the multichannel acquisition processor system, a computer-controlled 64-channel amplifier system (Plexon, Inc., Dallas, Tex., USA) providing programmable amplification, filtering, switching, and digital signal processing of microelectrode signals. The total system gain used was 10K with a simultaneous 40 kHz sampling rate. The signals routinely recorded by these neurochips are located in a range of 15-1800 microV.

The multichannel signal acquisition system delivered single neuron spike data. Spike identification and separation were accomplished with a template-matching algorithm in real time. This allows for the extracellular recording from action potentials from a maximum of 256 neurons simultaneously.

The action potentials, or spikes, were recorded in spike trains and are clustered in so-called bursts. Bursts were quantitatively described via direct spike train analysis using the program NeuroEXplorer (Plexon Inc., Dallas, Tex., USA) and in house programs. Bursts were defined by the beginning and the end of short spike invents. Maximum spike intervals defining the start of a burst were 40 ms and maximum intervals to end a burst from 200 ms.

All compounds were recorded with a fixed DMSO concentration of 0.1% throughout the experiments. Due to the fact that alpha-lipoic acid was investigated at concentrations between 100 μM and 5 mM, the solvent concentration reached 0.7%. Hence, these vehicle concentrations were also tested in a separate experiment which serves as vehicle control. For DHA and hBDNF the DMSO concentration did not exceed 0.1%. Since alpha-lipoic acid was the limiting compound in terms of the required highest concentration of DMSO, Table 1 below shows the compound application scheme for alpha-lipoic acid.

TABLE 1

Compound Application scheme for alpha-lipoic acid.

| Compound conc. Working Solution | DMSO content in working solution | Applied Volume | Bath concentration compound (alpha-lipoic acid) | Final DMSO conc. |
|---|---|---|---|---|
| DMSO | 10% | 10 μL | 0 | 0.1% |
| 10 μM | 0.01% | 10 μL | 100 nM | 0.1% |
| 100 μM | 0.1% | 9 μL | 1 μM | 0.1% |
| 1 mM | 1% | 9 μL | 10 μM | 0.1% |
| 10 mM | 10% | 9 μL | 100 μM | 0.2% |
| 1 M | 100% | 0.9 μL | 1 mM | 0.3% |
| 1 M | 100% | 2 μL | 3 mM | 0.5% |
| 1 M | 100% | 2 μL | 5 mM | 0.7% |

A precipitation of alpha-lipoic acid occurred at the three highest concentrations while using the 1 M stock concentrations was observed. Neither of the other compounds showed this during dilution. Working solutions of all compounds were freshly prepared for each experiment day and between 0.9 and 10 μL were applied to a 1 mL experiment bath solution.

The high content analysis of the network activity patterns provides a multiparametric description characterized in four activity categories: general activity, burst structure, synchronicity and oscillatory behavior. For example, the general activity includes, but is not limited to, the spike rate, burst rate, burst period, percent of spikes in burst, and combinations thereof. The burst structure includes the number, frequency and ISI of spikes in bursts, burst duration, amplitude, area, plateau position, and plateau duration. Synchronicity is generally described as the variation within the network as an indicator for the strength of the synchronization, including, but not limited to, simplex synchronization and percent of units in a synchronized burst. Osillatory behavior or oscillation includes the variation over time as an indicator for the strength of the oscillation. This includes but is not limited to Bagor function parameters fitted to autocorrelograms.

From the spike trains, a total of 200 activity-describing spike train parameters for these four categories were determined. All compound-induced network activity was normalized to the related spontaneous native activity, set at 100% for each experiment. Values were derived from 60 sec bin data taken from a 30 minutes span after a 30 min stabilization of activity. From each network 14-72 separate neurons were simultaneously recorded. Additionally concentration-response curves were calculated for all the test compounds and vehicle controls on a core set of 60 parameters describing the four categories general activity, burst structure as well as the oscillatory and synchronicity behavior.

For this example, "unit" generally refers to a unit of activity originating from one neuron recorded at a single electrode. Generally, units are separated at the beginning of the recording.

To define each burst, there are several algorithms implemented in NPWaveX for burst detection. For example, in some examples the Nex ISI method, implemented in the Neuroexplorer Softward, and uses interspike intervals were first implemented to define a burst with the above parameters. An integration method using both fast and slow integration as defined by Guenter Gross and others was utilized to identify the intersection of fast and slow integration curves, thereby defining the start and end of a burst. Burst surprise, which uses the unlikelihood of events of a close spike sequence in comparison to a Poisson process, was also utilized to identify the characteristics of a burst. Additionally, burst definition was further calculated and identified by sum function, which transforms a spike train into a continuous function.

Bursts were defined by the following parameters for the Nex ISI method: maximal interspike interval in burst is 0.04 ms, maximum end interval is 200 ms, minimum interval between bursts is 100 ms, minimum duration of burst is 0.0001 s, and the minimum number of spikes in a burst is 2.

As used in the example the "Coefficient of variation" or "CV" is the quotient of standard deviation and mean value.

"CVtime" reflects the temporal regularity of the activity pattern for each unit. CVtime is calculated by the ratio of parameter's standard deviation and mean. CVtimes are averaged across the network. Low CVtime values indicate a more regular spike train patter, meaning stronger oscillation.

"CVnet" reflects the synchronization among neurons within the network. CVnet is calculated by the ratio of parameter's standard deviation by mean over the network. Large CVnet values imply a wide range of variation in the activity across the network, meaning less synchronization.

FIG. 1 illustrates some of the burst parameters. The burst parameters are further defined herein.

Figure 2:
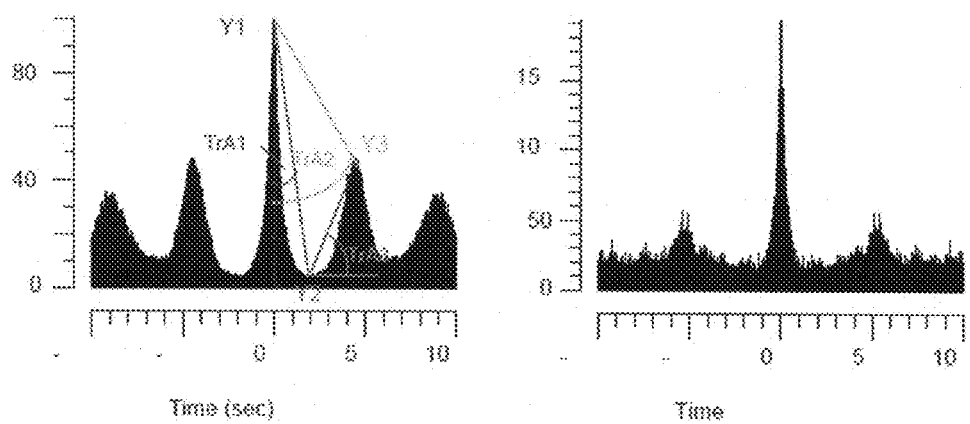
FIG. 2 illustrates autocorellograms from two different units in a network.

Autocorellograms are generated from spike train data for each unit. See FIG. 2. Autocorellograms are defined by the peak amplitude (shown in FIG. 2 as Y1) of the relating burst and the minimum between first and second peak (shown in FIG. 2 as Y2), defined by number of interburst spikes and the next peak (shown in FIG. 2 as Y3), defined by the next consecutive burst. Accordingly, three different angles are calculated. For example, low Y2 is a measure for low interburst spiking. The left autocorellogram, shown in FIG. 2, is an example for a unit exhibiting regular oscillatory spike train behavior.

Generally neuronal networks are characterized by a set of parameters describing the general activity of neurons. While the following categories do not directly correspond to categories known in neurobiology, the do, however, provide internal categories, which provide general orientation. Accordingly, a higher granularity is possible.

The parameters included within the general activity category include, but are not limited to, the following: spike rate, burst rate, spike contrast, burst period, sum burst period, interburst interval, sum interburst interval, burst surprise, percentage of spikes in bursts, event rate, and event period. These parameters are further defined herein.

The "spike rate" abbreviated "SpRate" is the number of spikes per minute, averaged over all spike trains recorded.

The "burst rate" abbreviated "BrstRate" is the number of bursts per minute, a measure for the number of burst for each unit, averaged over all units recorded.

The "spike contrast" abbreviated herein as "SpCont" describes the occurrence or absence of spikes in neighboring time segments of the spike train, reflecting the variability in burstiness of units within experimental episodes.

The "burst period" abbreviated herein "BrstPer" is the distance between the beginning of consecutive bursts. Burst period is equal to burst duration plus burst IBI.

"Sum Burst Period", abbreviated herein as "SummeBrstPer" is the distance between consecutive bursts, including burst detection performed on sum function. SumBurst it is another technique to detect bursts. Generally the burst period is equal to burst duration plus burst IBI.

"Interburst interval" abbreviated herein as "BrstIBI", is the time between consecutive bursts estimated from end of preceding burst to start of following burst. For this example, the interburst intervals are measured in milliseconds (ms).

"Sum interburst interval" abbreviated herein as "SumBrstIBI" is burst detection performed on a sum function algorithm.

"Burst surprise" abbreviated herein as "BrstSrp" is a measure for the non-randomness of spike distribution. Units with high burst activity and low number of interburst spikes reveal higher values for burst surprise. A burst surprise of 0 reflects a Poisson-distribution of interspike intervals (ISI are described by an exponential function).

"Percentage of spikes in bursts" abbreviated herein as "BrstPercSpinBrst" is the percentage of spikes within bursts in relation to all spikes recorded within the experimental episode.

"Event rate" abbreviated as "EvRate" is the number of events per minute. Event is defined as synchronous burst activity of at least 50% of all units in a network within a time frame of 300 ms.

"Event period" abbreviated herein as "EvPrd" is the distance between consecutive burst events, including but not limited to, synchronous bursts in at least 70% of units in network within 300 ms timeframe.

The parameters included within the burst structure category include, but are not limited to, the following: burst duration, burst amplitude, burst area, burst spike number, maximal spike rate in bursts, burst interspike interval, burst peak frequency, burst spike density, burst spike rate, burst plateau, burst shape slow, burst shape fast, burst shape multiple, burst shape distance 3, burst shape triangle 3, burst shape count 3, burst shape Y3/Y1, burst plateau position, and burst plateau fraction. These parameters are further defined herein.

Burst duration abbreviated herein "BrstDur" mean the length of bursts as detected based on an integration algorithm. In this example, burst duration is measure in milliseconds (ms).

Burst amplitude abbreviated herein "BrstAmpl" are bursts that are mathematically superimposed with an integral function. The integral is defined by spike peak density in bursts and number of spikes. Burst amplitude is the peak amplitude of the integrated burst reflecting the fraction of the bursts with highest spike density.

Burst area abbreviated herein as "BrstArea" is the area under the curve after integrating the bursts, defined by burst duration, number of spikes in bursts, spike frequency in bursts.

Burst spike number abbreviated herein "BrstSpNmbr" is the mean number of spikes within bursts.

Maximal spike rate in bursts abbreviated herein as "BrstSpMaxRate" is the maximum spike rate within a burst, computed with a binning method.

Burst interspike interval abbreviated herein "BrstISI" is the mean time between consecutive spikes in bursts.

Burst peak frequency abbreviated herein "BrstPeakFrq" is the mean of peak spike frequency within bursts (Hz), defined by the shortest distance (time) between two consecutive spikes in a burst.

Burst spike density abbreviated herein "BrstSpDens" is the mean frequency of spikes within bursts (Hz), defined by the average of all interspike intervals in a burst. Burst spike density increases if number of spikes in burst increases or burst duration decreases.

Burst spike rate abbreviated herein "BrstSpRate" is the mean spike rate within bursts.

Burst plateau, abbreviated herein "BrstPlat", is the duration of the burst plateau, depending on number and frequency of spikes within plateau phase of the burst which is following the peak amplitude. Burst plateau increases if number of spikes increases during the burst plateau phase.

Burst shape slow, abbreviated herein "ShSlow", is the classification of bursts a short, slow, multiple and/or fast. A slow burst indicates a burst with a slow onset of activity, a multiple burst has two clear maxima and a fast burst has a fast onset of activity. Burst shape slow is a measure for the fraction of bursts characterized by slow onset of activity.

Burst shape fast, abbreviated herein "ShFast" is a measure for the fraction of bursts characterized by fast onset of activity (high spike frequency at beginning of the burst).

Burst shape multiple, abbreviated herein "ShMult", is a measure for the fraction of bursts characterized by more than one frequency peak within the burst.

Burst shape distance 3, abbreviated herein "ShDist3", is the distance from burst start to second frequency maximum within a burst.

Burst shape triangle 3, abbreviated herein "ShTriangle3", is the spike train of a burst is mapped to a continuous function. Triangle3 is the slope from the coordinate of the minimum after the first maximum to the second maximum. A measure for burst shape, reflecting the existence and amplitude of a second peak maximum within burst.

Burst Shape Count 3, abbreviated herein "ShCount3", is where each burst is separated in three intervals by use of their gravitational centers. The count is the ratio of spikes of each of these intervals to the total number of spikes in each burst. Accordingly, this parameter describes the distribution of spikes within bursts.

Burst shape Y3/Y1, abbreviated herein "ShY3/Y1", describes the ratio of the second to the first peak frequency, provided bursts are characterized by two peaks.

Burst plateau position, abbreviated herein "BrstPlatPos", indicates the latency from start of the burst to beginning of burst plateau.

Burst plateau fraction, abbreviated herein "BrstPlatFrac", is the fraction percent of the burst plateau relative to the duration of the whole integrated burst, depending on burst peak amplitude, burst duration, spike frequency in burst. The value increases if bursts get more regular in their structure.

The parameters included within the oscillation or oscillatory behavior category include, but are not limited to, the following: spike rate SD, burst rate SD, burst amplitude SD, burst area SD, burst spike rate SD, burst plateau SD, maximal spike rate in bursts (SD), burst surprise SD, burst peak frequency SD, burst spike number SD, burst spike density SD, spike contrast SD, burst period SD, burst IBI SD, burst duration SD, burst plateau position SD, burst shape slow SD, burst shape fast SD, burst shape multiple SD, Gabor Y3/Y1, and Gabor Y1. These parameters are further defined herein.

Spike rate SD, abbreviated herein "SpRate SD", is the standard deviation of number of spikes per minute, indicating the variability of spike rate within the experimental episodes.

Burst rate (SD), abbreviated herein "BrstRate SD", is the standard deviation of number of bursts per minute, indicating the variability of burstiness of units within experimental episodes.

Burst amplitude (SD), abbreviated herein "BrstAmpl SD", is the standard deviation of peak amplitude of integrated bursts. Lower values reflect consistent burst structure over recording episode, therewith a more regular/oscillatory bursting behavior.

Burst area (SD), abbreviated herein "BrstArea SD", is the standard deviation of area under the curve after integrating the bursts, defined by burst duration, number of spikes in bursts, spike frequency in bursts. The parameter describes the variability of burst area within experimental episodes. Higher values indicate less regular burst structure.

Burst spike rate (SD), abbreviated herein "BrstSpRate SD" is the standard deviation of spike rate within bursts. Higher values indicate less regular burst structure.

Burst plateau SD, abbreviated herein "BrstPlat SD" is the standard deviation of burst plateau amplitude. Lower values reflect consistent burst structure over recording episode, therewith a more regular/oscillatory bursting behaviour.

Maximal spike rate in bursts (SD), abbreviated herein "BrstSpMaxRate SD" is the standard deviation of maximal spike rate in bursts. Lower values reflect a more consistent distribution of spike max rate over recording episode, therewith a more regular/oscillatory burst structure.

Burst surprise (SD), abbreviated herein "BrstSrpr SD", is the standard deviation of distribution of spikes in bursts or between bursts. A measure for the variability of spike distribution. Lower values reflect a more consistent distribution of spikes in bursts or interbursts, reflected by the value of burst surprise Burst peak frequency (SD), abbreviated herein "BrstPeakFrq SD", is the standard deviation of single unit spike peak frequency in bursts. Lower values are a measure for more regularity in Burst peak Frequency, therewith a higher degree of regular burst structure within experimental episodes.

Burst spike number (SD), abbreviated herein "BrstSpNmbr SD", is the standard deviation of spike number in bursts describes the variation of single unit spike number in bursts within experimental episodes. Lower values are a measure for lower degree of variation in burst spike number, therewith more regular burst structure.

Burst spike density (SD), abbreviated herein "BrstSpDens SD", is the standard deviation of burst spike density, reflecting the variability of spike frequency in all bursts of the network within experimental episodes.

Spike contrast (SD), abbreviated herein "SpCont S D", is the standard deviation of spike contrast, reflecting the variability in burstiness of units within experimental episodes.

Burst period (SD), abbreviated herein "BrstPer SD", is the standard deviation of burst period, reflecting the variation of single unit distances between consecutive bursts within experimental episodes. Lower values reflect higher regularity in burst structure.

Burst IBI (SD), abbreviated herein "BrstIBI SD", is the standard deviation of interburst interval, reflecting the variability of burst occurrence within experimental episodes.

Burst duration (SD), abbreviated herein "BrstDur SD", is the standard deviation of burst duration, reflecting the variability of burst duration within experimental episodes.

Burst plateau position (SD), abbreviated herein "BrstPlatPos SD", is the standard deviation of burst plateau position. Burst plateau position indicates the latency from start of the burst to beginning of burst plateau. Higher values of SD reflect a higher variability of burst structure within experimental episodes.

Burst shape slow (SD), abbreviated herein "ShSlow SD", is the standard deviation of the fraction of bursts characterized by slow onset of action. Higher values indicate a higher variability of burst shape within experimental episode.

Burst shape fast (SD), abbreviated herein "ShFast SD", is the standard deviation of the fraction of bursts characterized by fast onset of action. Higher values indicate a higher variability of burst shape within experimental episode.

Burst shape multiple (SD), abbreviated herein "ShMultSD", is the standard deviation of the fraction of bursts characterized by multiple frequency peaks in bursts. Higher values indicate a higher variability of burst shape within experimental episode.

Gabor Y3/Y1, abbreviated herein "gaborY3/Y1", is the ratio of second and first maximum amplitude of the autocorrelogram, fitted by Gabor function. Lower values indicate a higher regularity in burst occurrence.

Gabor Y1, abbreviated herein "gaborY1" is the first maximum amplitude of the autocorrelogram, fitted by Gabor function reflecting the number and frequency of spikes in bursts. Higher values are a measure for larger spike numbers and spike frequencies in bursts.

The synchronicity category typically refers to parameters displaying both the connectivity and synchronization between neurons in the cell culture, and how the connectivity and synchronization can be modified both during development and pharmacological treatment. Synchronicity describing parameters indicate changes in neuronal synchronization by use of coefficients of variation over network but for different burst describing parameters. The parameters included within the synchronicity category include, but are not limited to, the following: synchronicity share, burst synchronicity all, spike simplex, burst rate CVnet, percentage of spikes in bursts CVnet, burst peak frequency CVnet, burst area CVnet, Event period SD and spike rate CVnet. These parameters are further defined herein.

Synchronicity share, abbreviated herein "SynShare", is the average number of units involved in population bursts. Higher values reflect a higher degree of synchronicity between the units.

Burst synchronicity all, abbreviated herein "SynAll", is defined as average distance of bursts within a population burst from population burst center. SynAll is a measure for the strength of synchronicity of a network.

Spike simplex, abbreviated herein "SimplexSpSimplex", is a calculation where the spike trains are divided into timeframes of 1 ms bin-size. Within those bins different units within the network generate spikes. All units exhibiting a spike are defined as one simplex. The outcome of the quantity of all simplex is the Spike Simplex. It's a measure for connectivity and complexity in neuronal network. Higher values reflect higher synchronicity among neurons.

Burst rate (CVnet), abbreviated herein "BrstRateCVnet", is a reflecting variation of burst rate over the network during experimental episodes Percentage of spikes in bursts (CVnet), abbreviated herein "BrstPercSpinBrst CVnet" is the CVnet of percentage of spikes in bursts, reflecting the variation of fraction of spikes within burst intervals of all spikes within experimental episode over the whole network. Decrease of this parameters reflects an increase in synchronization within the network.

Burst peak frequency (CVnet), abbreviated herein "BrstPeakFrqCVnet", is the CVnet of spike peak frequency in bursts, reflecting the variation of peak frequency within experimental episodes over the whole network. Decrease of this parameters reflects an increase in synchronization within the network.

Burst area (CVnet), abbreviated herein "BrstArea CVnet", is the CVnet of area under the curve after integrating the bursts, defined by burst duration, number of spikes in bursts, spike frequency in bursts. The parameter describes the network variability of burst area within experimental episodes. Higher values indicate higher variability of burst structure among the network.

Event period (SD), abbreviated herein "EvPrdSD", is the standard deviation of event period, reflecting the variability of the distance between consecutive events (synchronous bursts in at least 70% of all units within 300 ms timeframes). Higher values are a measure for higher variability in event period lengths and reflect less synchronicity.

Spike rate (CVnet), abbreviated herein "SpRateCVnet", is the CVnet of spike rate, reflecting the network variability of spike rate within experimental episodes. Decrease of this parameter indicates an increase in synchronization within the network.

The parameters described herein of the four categories: general activity, burst structure, synchronicity and oscillatory behavior, deliver most of the information relating to the influence of test agent on the overall network activity. Moreover, these parameters are significantly affected by the majority of compounds known to affect neuronal networks, and have been shown to be the most descriptive parameters within these four activity-describing groups for prospective test compounds. For visualization, all significant changes for a set of 60 activity describing parameters are plotted in a heat map. The heat maps, herein, include the color coded information about the percentage of the changes in a single parameter. Only statistically significant activity changes are color coded (p≤0.05).

Additionally, the half maximal effective concentrations were calculated for the test compounds disclosed herein based on the data from the 60 parameters. Concentration response data were analyzed using a on-sigmoidal or multiphasic-sigmoidal regression analysis by fitting to the following equation: $y = y_{START} + (y_{END} - y_{START})/(1 + 10^{[log(EC50) - log(x)]*HC})$. The values determined include the effective concentration causing a 10%, 50%, and 90% of maximal activity ($EC_{10}$, $EC_{50}$, and $EC_{90}$). Generally the effective concentration is $EC_{50}$ known to affect the activity at a given parameter in comparison with the maximum effect. Here the parameter affected is the spike rate. The $EC_{50}$ corresponds to the concentration where 50% of the effect is achieved. For example, the increase at 100 µM of DHA/ALA treatment increased the activity to approximately 107% of native activity. 50% of this effect was reached at a concentration of 19.4 µM of ALA, accordingly the $EC_{50}$ for this example is at a concentration of 19.4 µM ALA.

Therefore, in certain embodiments, the maximum effect is extrapolated in the event that the experiment stops at a presumable lower concentration thatn the maximum concentration. Accordingly the equation for computing the $EC_{50}$ values herein is: $y = y_{START} + (y_{END} - y_{START})/(1 + 10[log(EC50) - log(x)]*HC)$. Additionally, the slope of the fitted concentration-response curve, i.e. the Hill coefficient, nH, was calculated. The results, i.e. parameter values, are expressed as mean+−SEM of independent networks. The absolute parameters' distributions were tested for normality. The statistical significance of a compound-induced effect on native cortical activity was assessed by the paired Student's t-test, and the effects of the test compounds versus vehicle-induced effects were assessed by the unpaired Student's t-test. For these calculations, P<0.05 was considered statistically significant.

Figure 3A:
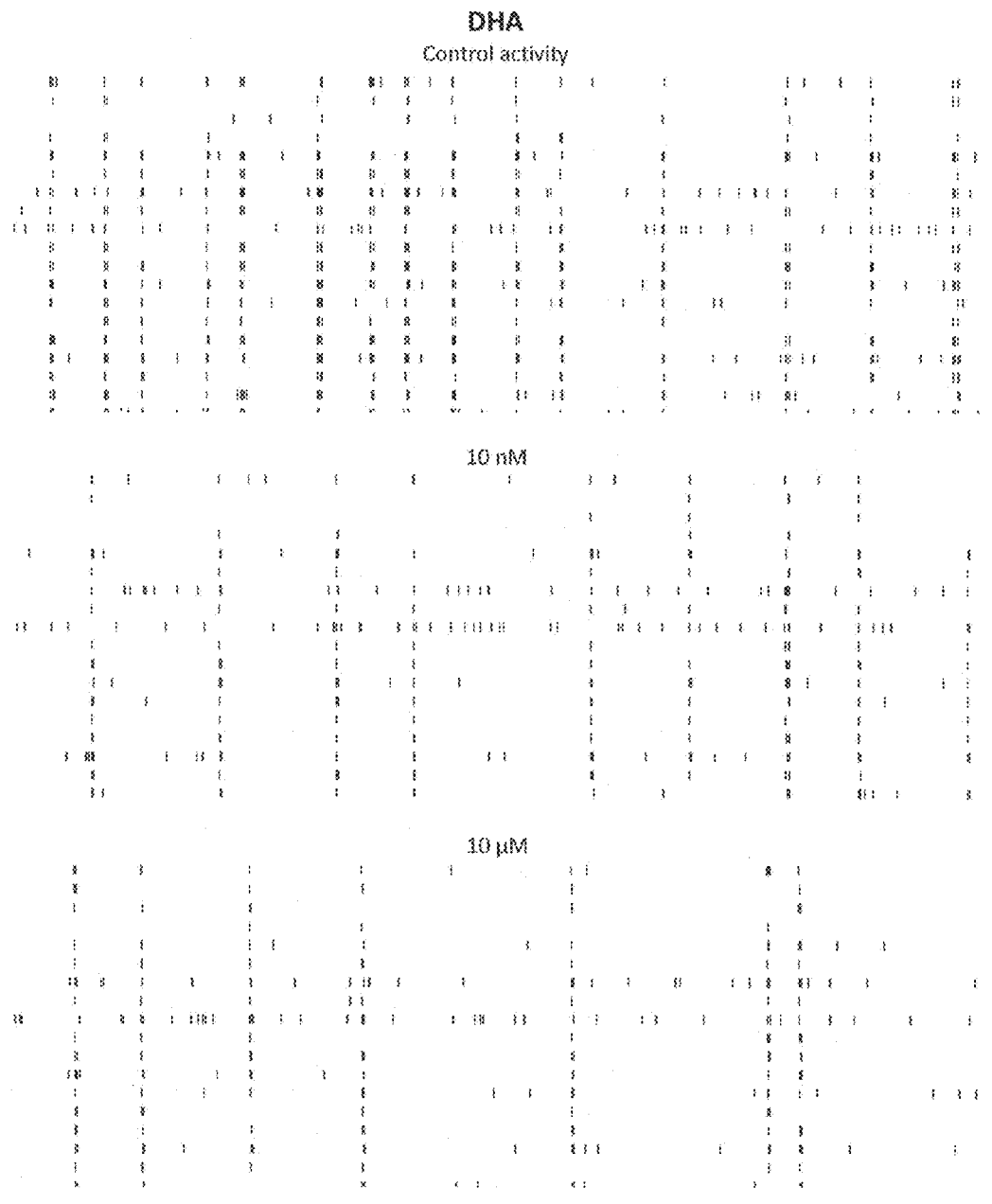
Figure 3B:
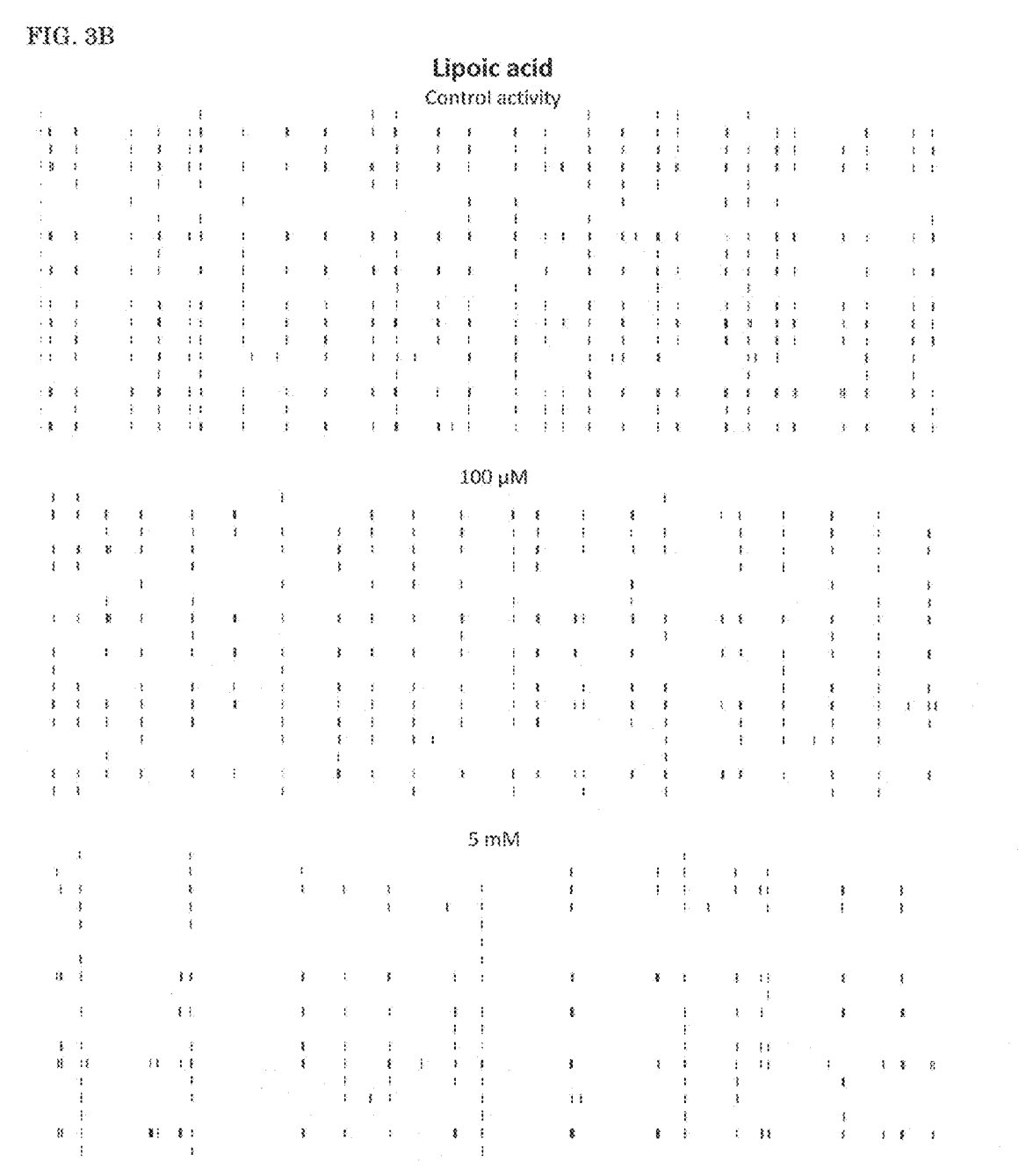

Both, DHA and ALA affect neuronal network patterns when acutely applied in a concentration-response experiment. The qualitative assessments of those effects are depicted in FIGS. 3A & 3B. Briefly, ALA decreases the overall activity between an experimental concentration of 100 µM and 5 mM. A decrease of overall activity means precisely a decrease of spike rate and burst rate. To describe the effect independently of the physical parameter we speak of overall activity as a phenomenon.

Figure 4:
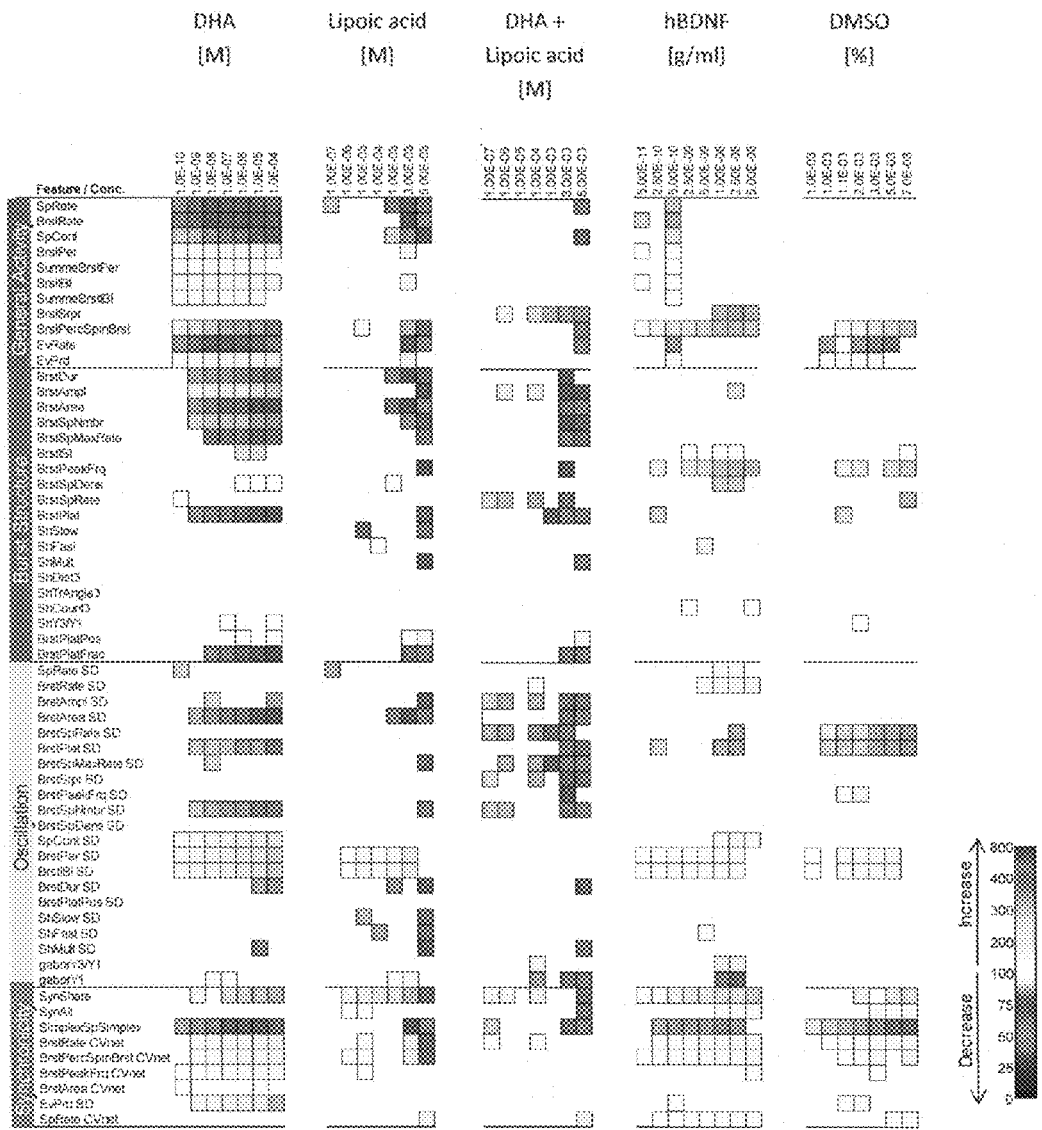
FIG. 4 displays a qualitative comparison of effects induced by DHA, ALA, a combination of DHA and ALA, hBDNF and the vehicle DMSO in a concentration-dependent manner on the cortical network activity in vitro.

The quantitative description of 60 parameters shown in FIG. 4 supports the qualitative view. The compound-induced effects on the cortex culture activity and the data obtained in the study are presented by visualizing the 60 main activity describing parameters and parts thereof by heat maps, concentrations-response curves and feature charts.

DHA reduces spike rates and burst rates at concentrations as low as 100 pM with increasing effects at higher concentrations. Burst period and interburst interval are shown as increasing, which supports the reduction in burst occurrence.

ALA also reduces general activity, but only at experimental concentrations of 1 mM and higher. DMSO, which is higher than 0.1% at these concentrations does not induce changes in general activity parameters such as spike rate or burst rate. Burst structure describing parameters such as burst duration or burst area were also affected at the highest ALA concentrations tested.

The heatmaps of FIG. 4 include the color-coded information about the percentage of the changes in the single parameters. For FIG. 4, only statistically significant activity changes are color-coded (at least p≤0.05). Further, illustrated in FIG. 4 are heat maps with significant changes on the 60 most representative parameters for each concentration. The activity parameters characterize the substance-specific activity changes in the 4 main categories: general activity, burst structure, oscillatory behavior and synchronization for treatment of 7 accumulating concentrations. The color code changes in activity parameters are based on percent changes.

Figure 5:
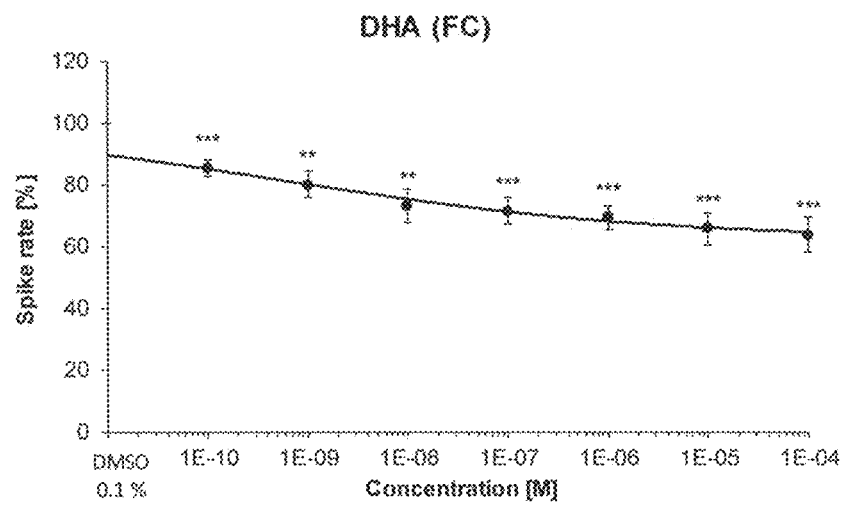
FIG. 5 displays a fitted curve for DHA with calculated slope (Hill coefficient, nH). At the highest tested concentrations of 100 μM DHA the activity decline reached 63.6% of native activity.

Both, DHA and ALA exhibit acute effects on the neuronal network activity. Yet, the neuroactive range differs dramatically. DHA decreases the general activity already at very low concentrations, see FIG. 5, and continuously decreases the activity. Hence, the neuroactive range for DHA is comparably wide, as compared to ALA, ranging from nanomolar to micromolar concentrations.

Figure 6:
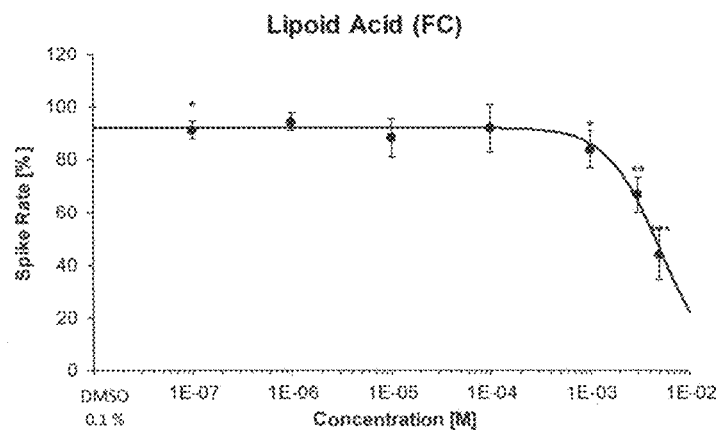
FIG. 6 displays effective concentration for alpha-lipoic acid causing 10 and 50% activity change ($EC_{10}$ and $EC_{50}$) and slope (Hill coefficient, nH). At 100 μM alpha-lipoic acid the activity reached 91.5%, at 1 mM 83.6% and at 5 mM 43.9% of control (0.1% DMSO) activity.
Figure 8:
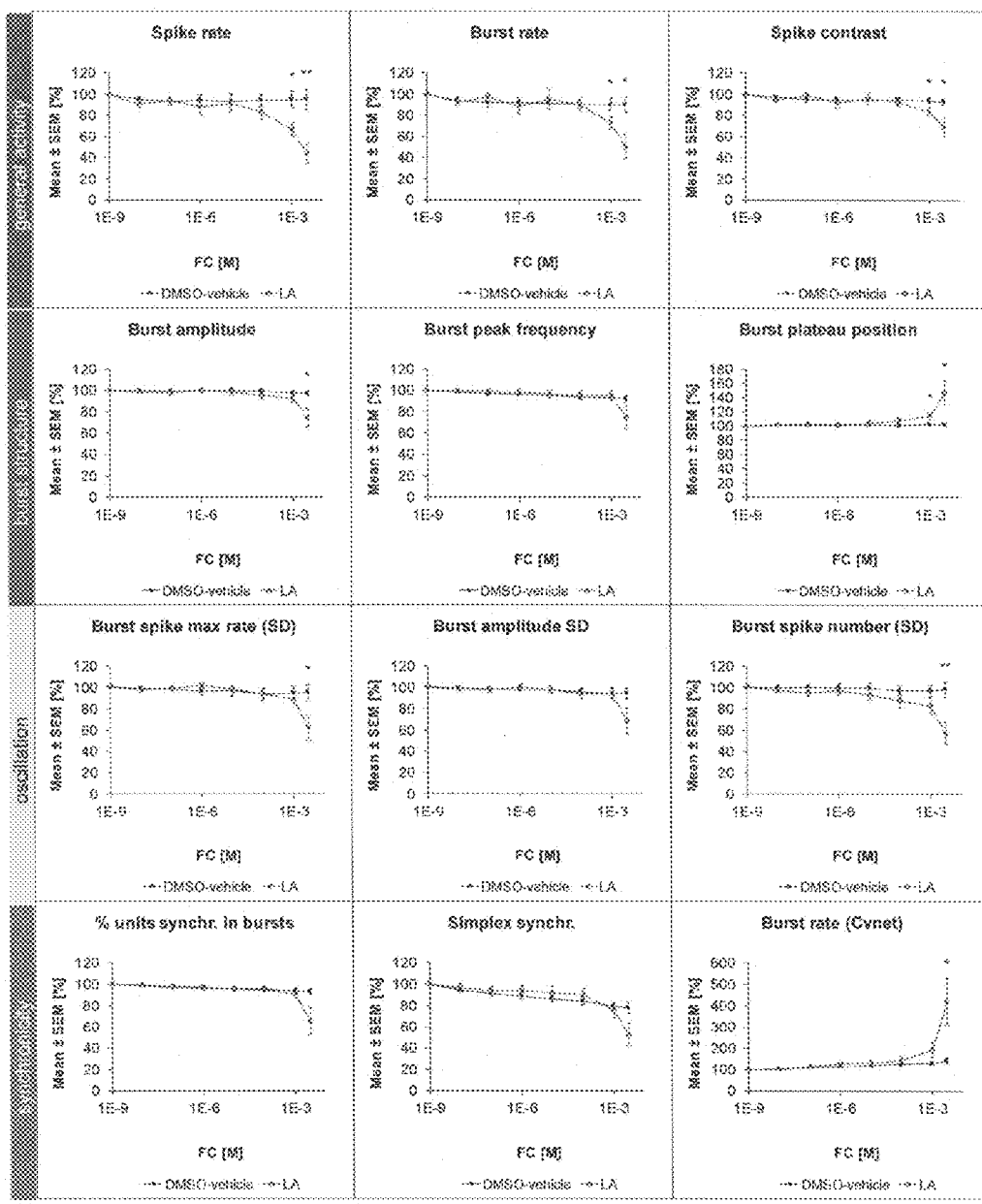
FIG. 8 shows the comparison of effects of DMSO versus DHA on the cortical network activity in vitro. Displayed are 12 activity describing parameters in 4 categories for treatment of 9 accumulating concentrations in ranges from 100 pM to 100 μM (mean±standard error, Student's unpaired t-test: * $p\leq0.05$;  $p\leq0.01$; * $p<0.001$).

ALA affects the general activity, as shown by the spike rate fit in FIG. 6, at concentrations above 100 µM. The tests of this concentration range were performed with a stock concentration of 1 M in 100% DMSO. ALA partly precipitated when diluted to the final concentration. Therefore, it cannot be excluded that the precipitate affected the network through unknown mechanisms. Moreover, the DMSO concentration reached a value of 0.7% during cumulative substance addition. Therefore, weak DMSO effects should be taken into account although the direct comparison, see. FIG. 8, shows significant substance-specific effects for ALA.

Comparing DHA and ALA, both fatty acids induce changes in the same direction but in different concentration ranges. DHA has a wider activity range than ALA. For example, the activity range for ALA was rather limited to concentrations above 100 µM. However, the effects induced by ALA are stronger than those by DHA. For example, the maximum parameter effect sizes are affected differently by ALA and DHA. At the highest tested concentration of ALA and DHA, 5 mM and 100 µM, respectively, ALA exhibited numerically stronger effects in all four activity categories than did DHA.

Figure 7:
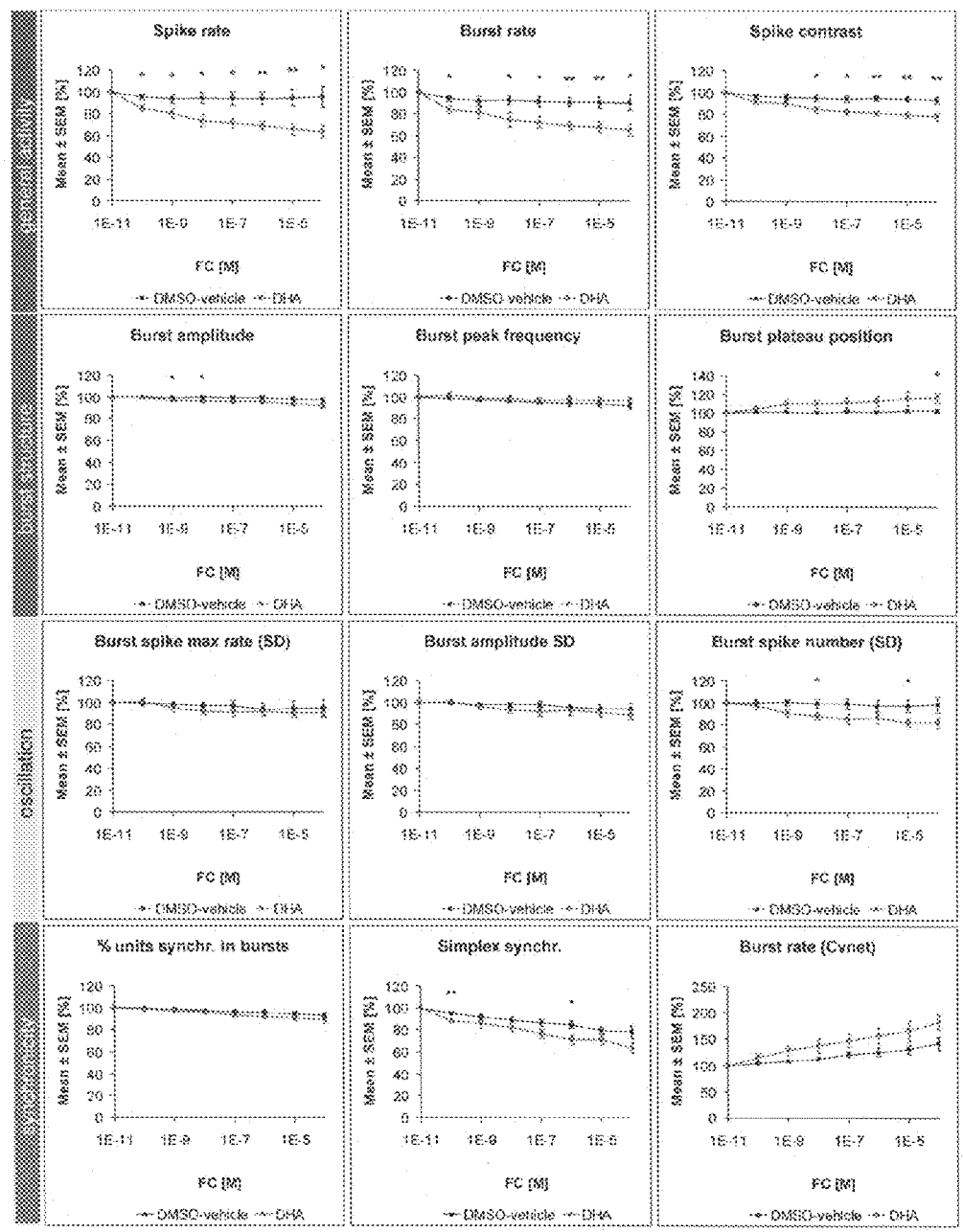
FIG. 7 displays the comparison of effects of DMSO vs. DHA on the cortical network activity in vitro. Displayed are 12 activity describing parameters in 4 categories for treatment of 9 accumulating concentrations in the range from 100 pM to 100 μM (mean±standard error, Student's unpaired t-test: * $p<0.05$;  $p<0.01$; * $p<0.001$).

The functional differences between the two fatty acids are shown in a variety of other parameters presented in FIGS. 7 and 8. DHA mainly affects the general activity throughout the concentrations range tested in this project, but only weakly affects burst structure, oscillation and synchronicity parameters, see FIG. 7. In summary, DHA induces a higher regularity of bursting events (as shown by decreased standard deviations of bursting parameters) while inducing asynchronicity into the network (as shown by less simplex synchronicity and a higher network variation of bursting events) in parallel to significantly decreasing the general activity (spike rate, burst rate, spike contrast).

The combination of DHA and ALA acid was performed by adding 20 µM DHA, pre-treatment before adding ALA, to the networks and cumulatively increasing the ALA concentration similarly to the single-treatment ALA experiment. Surprisingly, the previous addition of 20 µM DHA did not affect the network activity as previously discussed for the DHA concentration response curve (compare 10 µM DHA values in FIG. 7 versus 20 µM DHA pre-treatment in FIG. 11). Here, time-dependent effects of DHA are most likely the reason for this phenomenon. For example, the effects observed in cumulative concentration/response experiments are often different than those observed in single concentration experiments. Often times the direct addition of a test compound will result in a weaker effect than in a cumulatively increasing experiment, where there are multiple additions of a test compound. For this example, it was not investigated whether the single 20 µM DHA concentration finally reached the same effect size than in the cumulative/response experiment when followed for the same period of time. As such, this observation suggests that lower DHA concentrations might be sufficient to induce a neuroactive reaction which might be liked to different molecular kinetics at different concentrations.

Figure 9:
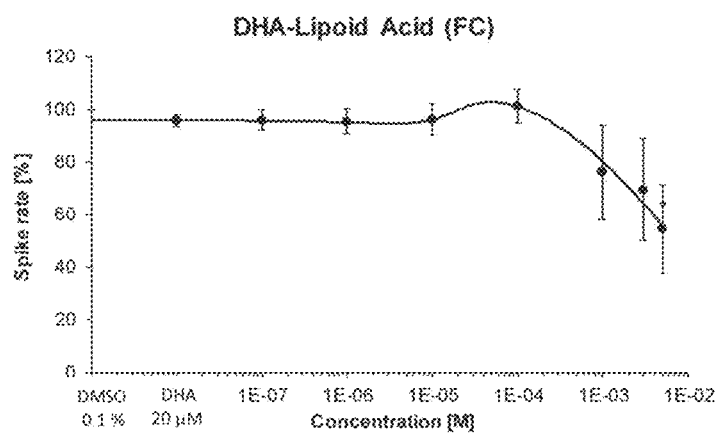
FIG. 9 shows the calculated effective concentration for a combination of DHA and ALA, which causes a 50%, activity change ($EC_{50}$).
Figure 10:
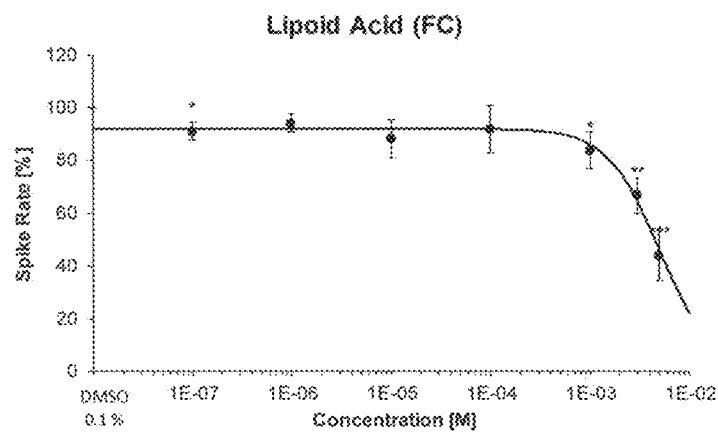
FIG. 10 shows the effective concentration for ALA causing a 10% and 50% activity change ($EC_{10}$ and $EC_{50}$).

Despite this discrepancy, DHA-pretreatment induced a different biphasic response to the addition of ALA. In this context, biphasic means that a parameter increase is then followed by a decrease. This biphasic behavior was mainly observed for the general activity parameters, including, but not limited to spike rate, burst rate, and spike contract. For example, between 10-100 µM ALA in combination with DHA induced a slight increase of general activity which led to an activity increase with an $EC_{50}$ of approximately 20 µM (See. FIG. 9). Additionally, the decline of activity at concentrations above 100 µM was much shallower than for ALA alone as indicated by calculated Hill coefficients of 0.54 and 1.66, respectively (the higher this value, the steeper the slope). The $EC_{50}$ values for the decline of activity were similar with 4.68 and 5.03 mM respectively (See. FIGS. 9 and 10). Remarkable is the soft incline of activity around 100 µM which is also present, and statistically validated in other parameter categories, See FIG. 11.

In summary, the effects of alpha-lipoic acid on bursting regularity, burst structure and oscillation are increased by the co-treatment with DHA. Hence, DHA adds a new component to the effect of alpha-lipoic acid. For this example, the assay is able to detect synergistic effects by multi-parametric analysis but does not necessarily deliver in vivo information. Here, the bi-phasic curve observed in the DHA and ALA experiments shows an activity-increasing effect between 10 and 100 µM ALA. This is neither observed for DHA alone, which experiences a decrease, nor for ALA alone, which provide no response. Thus, an increase of activity can be seen as completely new effect, which may be described as synergy.

This synergist effect of the combination of DHA and ALA is also seen for multiple other parameters as described herein. For example, the general activity parameters Spike rate, burst rate and burst surprise, the synchronicity parameters SynAll, Burst rate CVnet, Burst Percent spikes in burst CVnet as well as the oscillation parameters Burst Period SD, Burst IBI are significantly different and thus indicate the synergistic behavior. Yet, despite lack of statistical significance, the multiparametric projection, utilized herein, allows for the assessment of a multitude of parameters which are affected differently by the combination of DHA and ALA as compared to each compound alone. To emphasize this, it is not only a higher effect size, as this would be considered an additive effect, but a novel effect.

Figure 11:
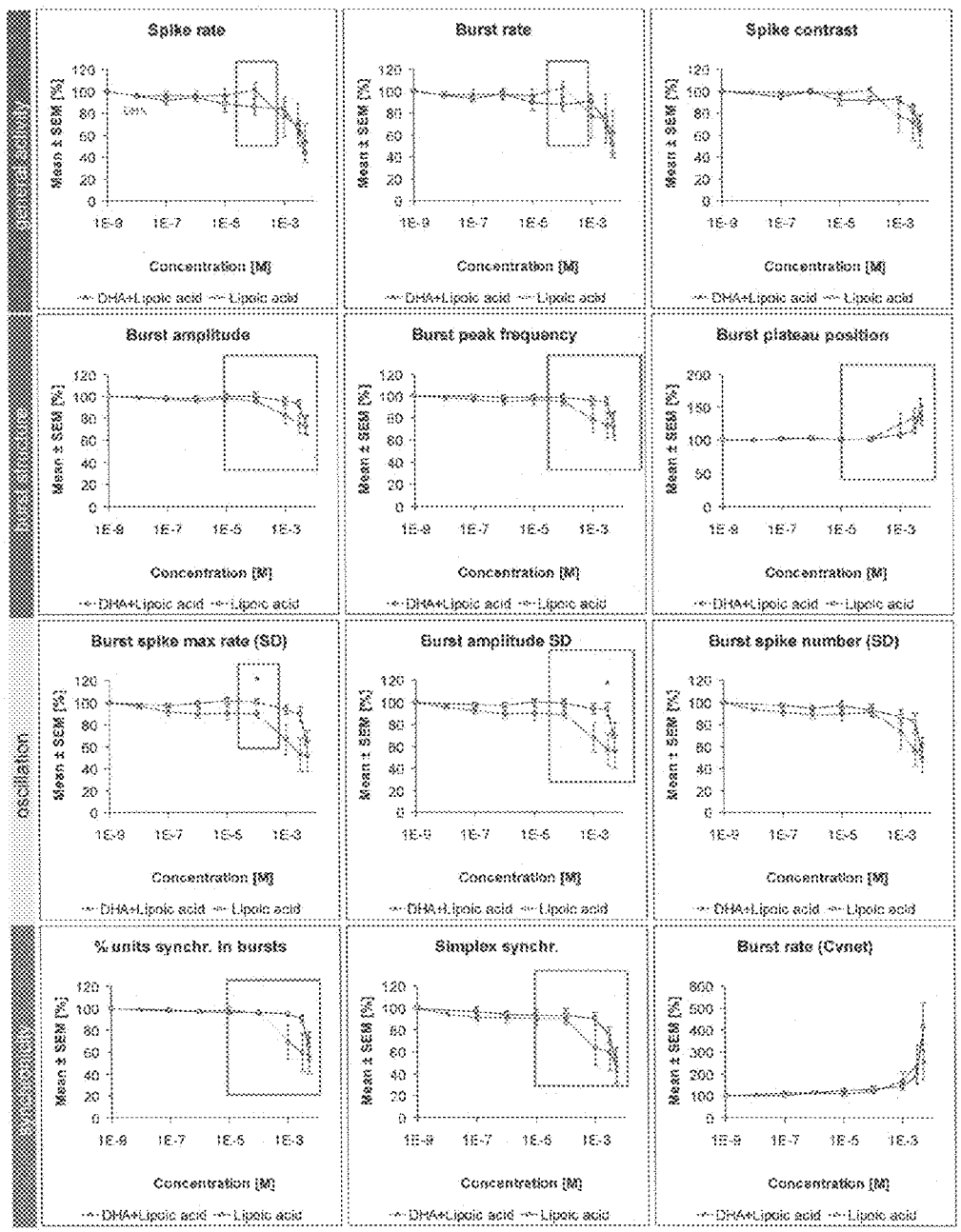
FIG. 11 illustrates the comparison of effects of DMSO vs. ALA on in vitro cortical network activity. Displayed are 12 activity describing parameters in 4 categories for treatment of 9 accumulating concentrations of ALA ranging from 10 nM to 5 mM.

Besides the slight increase in the general activity around 100 µM ALA when co-treated with 20 µM DHA, the effects on the regularity of bursting events is increased leading to a higher regularity at lower concentrations (burst spike max rate SD, burst amplitude). In parallel the synchronicity within the network is decreased (% units synchronized in bursts, simplex synchronicity) (See. FIG. 11). These increased effects show a synergistic behavior of DHA and ALA when co-applied because DHA alone does not affect burst structure, oscillation and synchronicity parameters as much as ALA.

Figure 12A:
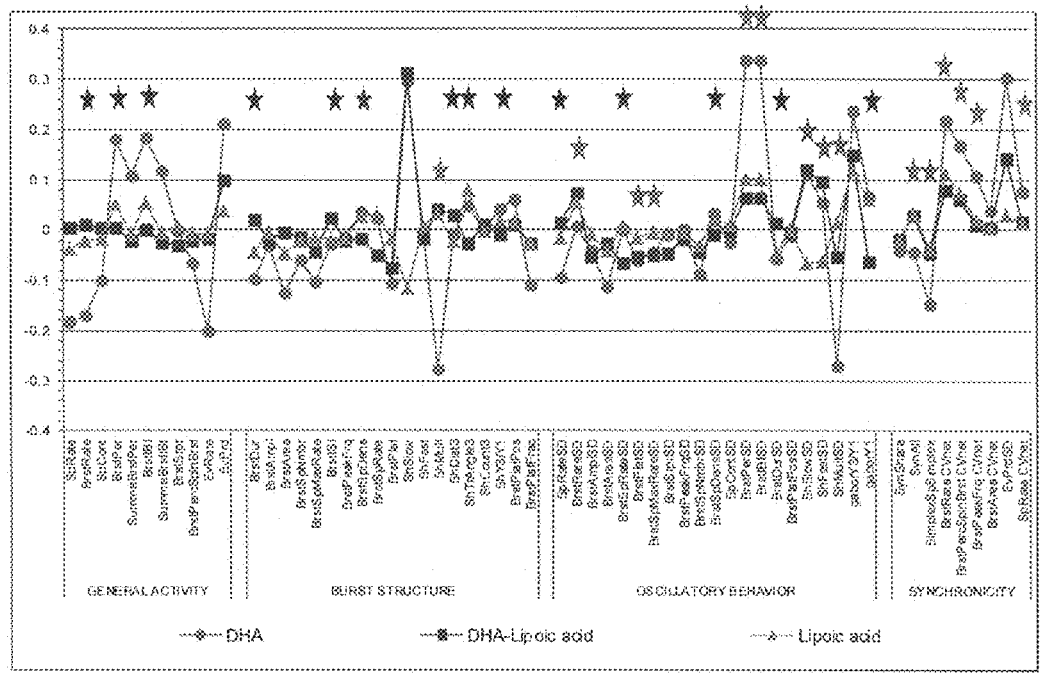
FIG. 12a illustrates feature charts for 100 μM ALA and the combination of 20 μM DHA and 100 μM ALA. Sixty parameters at one selected concentration indicate the similarities and differences for ALA alone and ALA in combination with DHA. From this figure, it can be seen that the mixture of DHA and alpha-lipoic acid induces different activity patterns in the categories of general activity, burst structure, oscillation and synchronicity.

In order to closer elucidate the differences between ALA as compared to a combination of ALA and DHA, 60 parameters are illustrated for one selected concentration of the concentration-response data set for 100 µM ALA. This selection is based on the slight activity-increasing effects of DHA in combination with ALA at 100 µM. This feature-chart projection allows a multi-parametric view on the data. At this concentration the functional differences between ALA versus DHA/ALA-treated activity patterns become evident, and demonstrates the synergistic effects of DHA when combined with ALA. For example, FIG. 12a shows the comparison of DHA 20 µM, ALA 100 µM, and DHA+ALA (20+100 µM). This illustration describes the direction of parameter change compared to control activity. For the combination of DHA and LA, the direction of parameter changes is opposite in multiple parameters (shown in FIG. 12a by a blue asterisk) indicating a synergistic effect induced by the combination. Some parameters are affected similarly to LA alone (shown in FIG. 12a by a green asterisk) and some are affected similarly to DHA (shown in FIG. 12a as a red asterisk) which indicates the weight of each compound of affecting the respective parameter.

As already mentioned, despite lack of statistical significance when compared to control levels, this multiparametric projection allows for the assessment of a multitude of parameters, which are affected differently by the combination of DHA and ALA as compared to each compound alone. To emphasize this, we did not only observe a higher effect size (this would be additive, as partially shown by green asterisks) but a novel effect (blue asterisks). Feature charts indicate 60 parameters for a combination of 20 µM DHA and 100 µM ALA versus 100 µM ALA and 20 µM DHA. See. FIG. 12a.

Figure 12B:
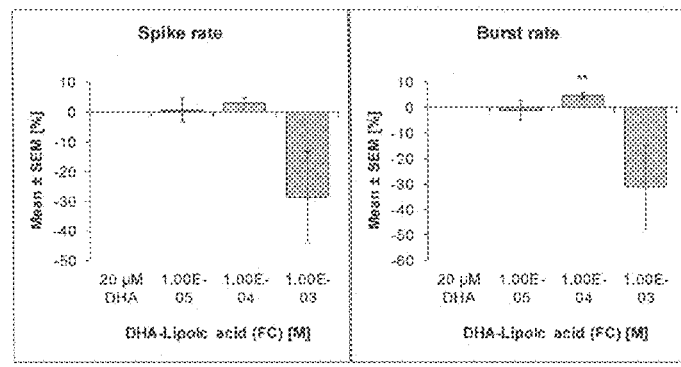
FIG. 12b illustrates stepwise projection for 10 µM DHA in combination with 100 µM ALA and for 1 mM ALA. The burst rate is significantly increased between the step from 10 µM ALA to 100 µM ALA.
Figure 12C:
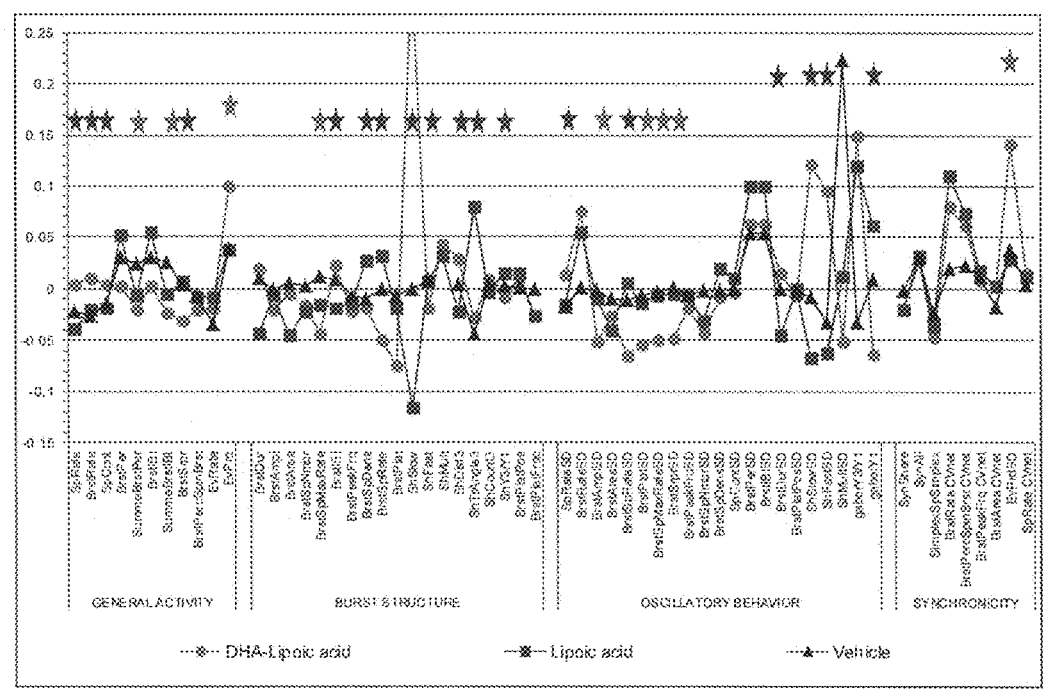
FIG. 12c illustrates an overview of the activity charts comparing a combination of DHA and Lipoic acid to Lipoic acid and a vehicle containing DMSO. The parameters are shown within the four general categories: general activity, burst structure, oscillatory behavior, and synchronicity.

Additionally, opposite effects were observed for certain parameters for the combination of DHA and ALA as compared to ALA alone as shown by the blue asterisks in FIG. 12c. Those parameters, which are strongly affected by the DHA and ALA combination are indicated by red asterisks. Thus, these opposite affects can be interpreted as complete synergy induced by the combination of DHA and ALA.

Figure 13:
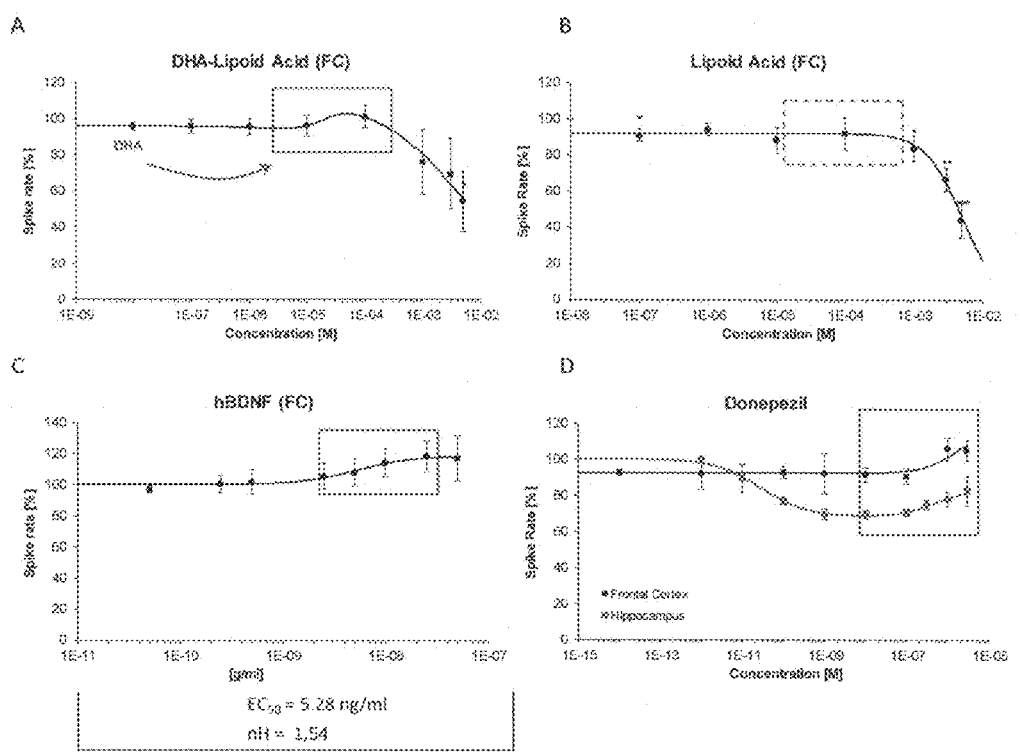
FIG. 13 illustrates an overview of activity charts of the combination of DHA and ALA (A), ALA (B), hBDNF (C) and the pro-cognitive drug donepezil (D). As can be seen from FIG. 11, the combination of DHA and ALA, hBDNF and Donepezil increase the neuronal network activity in certain concentration ranges.
Figure 14:
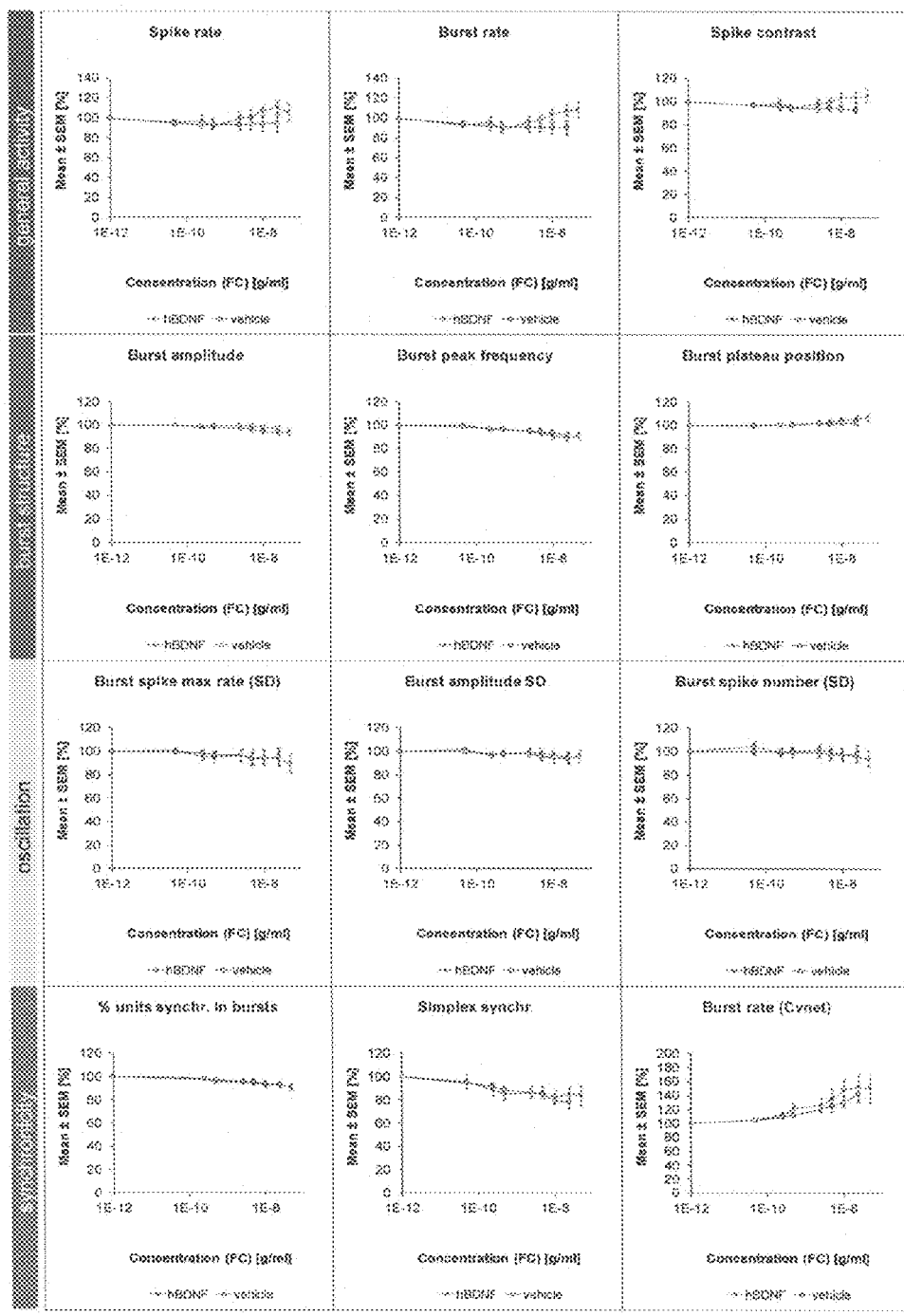
FIG. 14 illustrates the effect of hBDNF versus 0.1% DMSO vehicle on 12 activity-describing parameters in four categories and displays a snapshot of the activity changes induced by hBDNF.

The mixture of DHA and ALA induced a slight increase of general activity parameters between 10 µM and 100 µM (See. red rectangle, FIG. 13a) before decreasing the activity. This effect is rather mild and is only observed for the mixture of DHA and ALA and not for DHA or ALA alone (See. FIG. 13b). Yet, a stepwise statistical analysis indicates that the number of bursts is significantly increased between 10 µM and 100 µM ALA (See FIG. 12b). A similar increase of activity is also seen for hBDNF-treated networks between 1 ng/mL and 20 ng/mL (See red rectangle FIG. 13c). hBDNF itself increases only mildly the network activity (See FIG. 12). hBDNF is known to affect synaptic plasticity (1) which is also related to pro-cognitive function (See. Martire, A. et al., *BDNF prevents NMDA-induced Toxicity in Models of Huntington's disease: The Effects are Genotype Specific and Adenosine A(2A) receptor is involved*. J. Neurochem. 2013 Jan. 31. Doi: 10.11111/jnc.12177; see also, Pandya, C. D., et al., *BDNF-Trkβ Signaling and Neuroprotection in Schizophrenia*. Asian J. Psychiatr. 2013, February: 6(1)22-8). Additionally, the $EC_{50}$ value for hBDNF (5.28 ng/ml) on spike rate directly overlaps with the commonly used concentration range of 20 ng/ml applied in in vitro assays (e.g. 4).

Interestingly, this slight increase observed for the combination of DHA and ALA is also observed for the known cognition enhancer Donepezil within the therapeutic concentration of 100 nM-1 µM (internal data from NeuroProof, red rectangle, See. FIG. 13d), and hBDNF. For example, Donepezil induces an activity stimulation, which correlates with data on nootropic drugs, such as galanthamine and nefraicetam, which potentiate the activity of both nicotinic and NMDA receptors. (Moriguchi et al., 2005. J Pharmacol and Experiment. Theracol. 315: 125-135; Narahashi et al., 2004. Biol. Pharm. Bull. 27(11): 1701-1706). Here the acute effect of hBDNF and Donepezil are in agreement with the chronic effects that show activity enhancement. Thus, there is a correlation of activity enhancement for the combination of DHA and ALA. This effect is even more pronounced in hippocampus cultures.

Accordingly, despite the rather weak activity-increasing effect induced by the DHA/ALA mixture, this finding suggests that the experimental combination of 20 µM DHA and 100 µM ALA induce effects also seen for hBDNF or Donepezil.

Recombinant hBDNF was tested between 10 pg/mL and 50 µg/mL. Above concentrations of 500 pg/mL hBDNF only shows slight effects on the general activity which is numerically increased (See FIG. 7). Trophic factors, such as hBDNF, act through signaling events mediated by G Protein-coupled receptor systems ("GPCR") which require time. For hBDNF it is known that the downstream effects on synaptic plasticity are triggered within hours to days (Santos, A. R., et al., *Regulation of local translation at the synapse by BDNF*. Prog Neurobiol. 2010, December: 92(4): 505-516). Hence, acute effects on neuronal signal transmission are expected to be low within the tested time frame. Yet, this circumstance supports the fact that the reorganization of synapses requires time which is the reason to test the compounds DHA and ALA in a chronic fashion.

Figure 15:
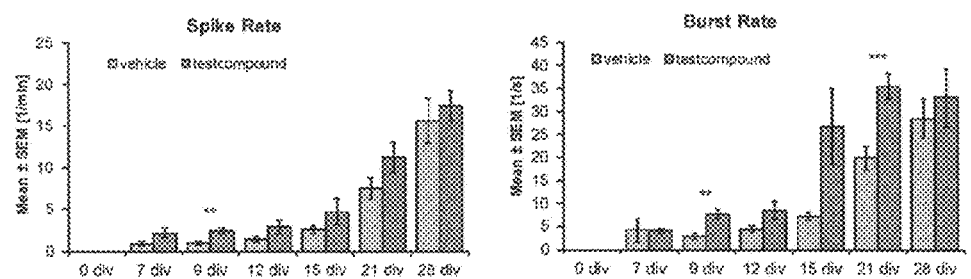
FIG. 15 illustrates the chronic effects of hBDNF versus a vehicle of BDNF and water on neuronal activity parameters spike rate and burst rate. hBDNF at 20 ng/ml increases the general activity at every recorded time point which can be translated into an accelerated neuronal activity development of approximately one week.

For neurotrophic factors such as hBDNF, NeuroProof tested the chronic effects in the MEA system (See FIG. 15). As shown in FIG. 15, this data suggests that hBDNF accelerates the development of neuronal activity.

Both DHA and ALA exhibit acute effects on neuronal activity profiles of cortical cultures as quantified by the MEA neurochip technology. Both DHA and ALA decrease the overall network activity and synchronicity of the network while ALA induces a more regular activity pattern It is known that the incorporation of fatty acids into cellular membranes increase the membrane's variability as a short term effect which could be putatively translated to the acute effects seen for DHA and ALA, such as a decrease of activity, asynchronicity, or higher regularity, which could be interpreted as the modulation of the cooperation between neurons. In the longer term, this incorporation of fatty acids into cellular membranes is known to support neurons and the connections between them. From the acute data described herein, chronic and putatively beneficial effects are harder to assess.

DHA is more potent than ALA, as DHA is active in the nanomolar range. This suggests that DHA might be used at lower concentrations, than presently known in the art, which could reduce costs, eventually. This is supported by the very shallow decline of activity since a similar effect size is obtained at lower concentrations. ALA is neuro-active in concentrations above 100 µM. Technically, concentrations above 1 mM result in vehicle concentrations above 0.1% which is a common limit for tests in neuronal cultures, especially in chronic treatments.

Pre-/co-treatment with DHA increases lipoic acid-mediated effects and further induces novel effects. The slight increase of activity induced by ALA only occurs under the influence of additional DHA. Moreover, the potency of lipoic acid is increased by DHA co-application which lowers costs and vehicle-mediated side effects. This means that DHA synergizes with lipoic acid which is also shown by novel effects around 100 µM where the activity parameters are slightly increased. These effects are also observed for BDNF and the pro-cognitive drug donepezil. Yet, the effects are weak which underlines the usability as a nutraceutical where strong effects are undesired.

Formulation Examples

Table 1 provides an example embodiment of a combination of ALA and DHA that may be incorporated or added to the nutritional compositions described herein. This example provides the amount of each ingredient to be included per 100 kcal serving of nutritional composition.

TABLE 1

Nutrition profile of an example formulation of ALA and DHA

| | per 100 kcal | |
|---|---|---|
| Nutrient | Minimum | Maximum |
| Alpha-lipoic acid (mg) | 3.7 | 37 |
| DHA (mg) | 5 | 75 |

Table 2 provides an example embodiment of a nutritional composition according to the present disclosure and describes the amount of each ingredient to be included per 100 kcal serving.

TABLE 2

Nutrition profile of an example nutritional composition

| Nutrient | per 100 kcal | |
|---|---|---|
| | Minimum | Maximum |
| Protein (g) | 1.8 | 6.8 |
| Fat (g) | 1.3 | 7.2 |
| Carbohydrates (g) | 6 | 22 |
| Prebiotic (g) | 0.3 | 1.2 |
| DHA (g) | 5 | 75 |
| Beta glucan (mg) | 2.9 | 17 |
| Alpha-lipoic acid (mg) | 0.1 | 35 |
| Lactoferrin (mg) | 10 | 250 |
| Probiotics (cfu) | $9.60 \times 10^5$ | $3.80 \times 10^8$ |
| Vitamin A (IU) | 134 | 921 |
| Vitamin D (IU) | 22 | 126 |
| Vitamin E (IU) | 0.8 | 5.4 |
| Vitamin K (mcg) | 2.9 | 18 |
| Thiamin (mcg) | 63 | 328 |
| Riboflavin (mcg) | 68 | 420 |
| Vitamin B6 (mcg) | 52 | 397 |
| Vitamin B12 (mcg) | 0.2 | 0.9 |
| Niacin (mcg) | 690 | 5881 |
| Folic acid (mcg) | 8 | 66 |
| Panthothenic acid (mcg) | 232 | 1211 |
| Biotin (mcg) | 1.4 | 5.5 |
| Vitamin C (mg) | 4.9 | 24 |
| Choline (mg) | 4.9 | 43 |
| Calcium (mg) | 68 | 297 |
| Phosphorus (mg) | 54 | 210 |
| Magnesium (mg) | 4.9 | 34 |
| Sodium (mg) | 24 | 88 |
| Potassium (mg) | 82 | 346 |
| Chloride (mg) | 53 | 237 |
| Iodine (mcg) | 8.9 | 79 |
| Iron (mg) | 0.7 | 2.8 |
| Zinc (mg) | 0.7 | 2.4 |
| Manganese (mcg) | 7.2 | 41 |
| Copper (mcg) | 16 | 331 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A method for accelerating neuronal activity in a target subject, comprising providing a nutritional composition comprising a carbohydrate source, a fat source, a protein source, docosahexaenoic acid, and alpha-lipoic acid to the target subject, wherein the alpha-lipoic acid is present in an amount of from about 0.1 mg/100 kcal to about 35 mg/100 kcal, and wherein the nutritional composition provides accelerated neuronal activity in the target subject.

2. The method of claim 1, wherein alpha-lipoic acid is present in an amount from about 10 mg/100 kcal to about 20 mg/100 kcal.

3. The method of claim 1, wherein docosahexaenoic acid is present in an amount from about 5 mg/100 kcal to about 75 mg/100 kcal.

4. The method of claim 1, wherein the nutritional composition further comprises sialic acid.

5. The method of claim 4, wherein sialic acid is present in an amount from about 0.5 mg/100 kcal to about 45 mg/100 kcals.

6. The method of claim 1, wherein the nutritional composition further comprises a prebiotic.

7. The method of claim 1, wherein the nutritional composition, when provided to the target subject, acutely affects neuronal activity patterns and strengthens electrochemical synapse connections in the target subject to whom the nutritional composition is provided.

8. The method of claim 1, wherein the nutritional composition further comprises arachidonic acid.

9. The method of claim 1, wherein the nutritional composition is an infant formula.

10. A method for accelerating the development of neuronal activity in a target subject comprising providing to the target subject a nutritional composition which comprises per 100 kcal:
   (i) between about 6 g and about 22 g of a carbohydrate source;
   (ii) between about 1 g and about 7 g of a protein source;
   (iii) between about 1.3 g and about 7.2 g of a fat source;
   (iv) between about 5 mg and about 75 mg of docosahexaenoic acid; and
   (iv) between about 0.1 mg and about 35 mg of alpha-lipoic acid.

11. The method of claim 10, wherein the nutritional composition further comprises per 100 kcal between about 0.3 g and about 1.2 g of prebiotic.

12. The method of claim 10, wherein the nutritional composition further comprises per 100 kcal between about 0.5 mg and about 45 mg of sialic acid.

13. The method of claim 10, wherein the nutritional composition further comprises per 100 kcal between about 10 mg and about 250 mg of lactoferrin.

14. The method of claim 10, wherein the nutritional composition further comprises a culture supernatant from a late-exponential growth phase of a probiotic batch-cultivation process.

15. A method for promoting electrochemical synapse signaling in a target subject, comprising providing to a target subject, a nutritional composition comprising a carbohydrate source, a protein source, a fat source, docosahexaenoic acid, and alpha-lipoic acid, wherein alpha-lipoic acid is present in an amount of from about 0.1 mg/100 kcal to about 35 mg/100kcal, and wherein the nutritional composition promotes electrochemical synapse in the target subject.

16. The method of claim 15 wherein the nutritional composition further comprises arachidonic acid.

17. The method of claim 15, wherein the target subject is a pediatric subject.

18. The method of claim 15, wherein the nutritional composition is an infant formula.

19. The method of claim 15, wherein nutritional composition further comprises lactoferrin.

* * * * *